(12) United States Patent
Liu et al.

(10) Patent No.: US 7,256,207 B2
(45) Date of Patent: Aug. 14, 2007

(54) INHIBITORS OF CATHEPSIN S

(75) Inventors: Hong Liu, San Diego, CA (US); Phillip B. Alper, Poway, CA (US); Donald S. Karanewsky, Escondido, CA (US)

(73) Assignee: IRM LLC, Hamilton (BM)

( * ) Notice: Subject to any disclaimer, the term of this patent is extended or adjusted under 35 U.S.C. 154(b) by 444 days.

(21) Appl. No.: 10/922,362

(22) Filed: Aug. 18, 2004

(65) Prior Publication Data

US 2005/0107368 A1 May 19, 2005

Related U.S. Application Data

(60) Provisional application No. 60/496,858, filed on Aug. 20, 2003.

(51) Int. Cl.
*A61K 31/415* (2006.01)
*C07D 235/00* (2006.01)
*C07D 403/02* (2006.01)

(52) U.S. Cl. ............. 514/385; 514/387; 548/304.4; 548/306.1

(58) Field of Classification Search ........... 548/306.1, 548/304.4; 514/387, 385
See application file for complete search history.

(56) References Cited

U.S. PATENT DOCUMENTS

| | | | |
|---|---|---|---|
| 4,499,295 A | 2/1985 | Mueller et al. | |
| 5,374,623 A | 12/1994 | Zimmerman et al. | |
| 5,574,064 A | 11/1996 | Shibata et al. | |
| 5,691,368 A | 11/1997 | Peet et al. | |
| 5,723,469 A | 3/1998 | Shibata et al. | |
| 5,849,711 A | 12/1998 | Tung et al. | |
| 5,858,982 A | 1/1999 | Tung et al. | |
| 5,859,025 A * | 1/1999 | Wagner et al. ........ | 514/311 |
| 5,916,887 A | 6/1999 | Singh et al. | |
| 5,998,470 A | 12/1999 | Halbert et al. | |
| 6,004,933 A | 12/1999 | Spruce et al. | |
| 6,030,946 A | 2/2000 | Klaus et al. | |
| 6,057,362 A | 5/2000 | Yamashita | |
| 6,232,342 B1 | 5/2001 | Carr et al. | |
| 6,274,336 B1 | 8/2001 | Abdel-Meguid et al. | |
| 6,331,542 B1 | 12/2001 | Carr et al. | |
| 6,353,017 B1 | 3/2002 | Altmann et al. | |
| 6,369,077 B1 | 4/2002 | Marquis et al. | |
| 6,395,897 B1 | 5/2002 | Cywin et al. | |
| 6,420,364 B1 | 7/2002 | Emmanuel et al. | |
| 6,455,502 B1 | 9/2002 | Bryant et al. | |
| 2004/0127426 A1 | 7/2004 | Graupe et al. | |

FOREIGN PATENT DOCUMENTS

| | | |
|---|---|---|
| WO | WO 98/00171 A2 | 1/1998 |
| WO | WO 98/50534 A1 | 11/1998 |
| WO | WO 00/48993 A1 | 8/2000 |
| WO | WO 00/51998 A1 | 9/2000 |
| WO | WO 01/09110 A1 | 2/2001 |
| WO | WO 01/19816 A1 | 3/2001 |
| WO | WO 02/14314 A2 | 2/2002 |
| WO | WO 02/14317 A2 | 2/2002 |
| WO | WO 02/14315 A2 | 3/2002 |
| WO | WO 02/051983 A2 | 7/2002 |
| WO | WO 02/069901 A2 | 9/2002 |
| WO | WO 02/070517 A2 | 9/2002 |
| WO | WO 02/070519 A1 | 9/2002 |
| WO | WO 03/013518 A1 | 2/2003 |
| WO | WO 03/020287 A2 | 3/2003 |

OTHER PUBLICATIONS

Bania, J. et al.: "Human cathepsin S, but not cathepsin L, degrades efficiently MHC class II-associated invariant chain in nonprofessional APCs" PNAS; vol. 100, No. 11; pp. 6664-6669 (May 27, 2003).

* cited by examiner

*Primary Examiner*—Rebecca Anderson
*Assistant Examiner*—Susannah Chung
(74) *Attorney, Agent, or Firm*—Emily Tongco Wu; The Genomics Institute of the Novartis Research Foundation

(57) ABSTRACT

The present invention provides compounds, compositions and methods for the selective inhibition of cathepsin S. In a preferred aspect, cathepsin S is selectively inhibited in the presence of at least one other cathepsin isozyme. The present invention also provides methods for treating a disease state in a subject by selectively inhibiting cathepsin S.

11 Claims, 1 Drawing Sheet

INHIBITORS OF CATHEPSIN S

CROSS-REFERENCE TO RELATED APPLICATIONS

This application claims priority to U.S. patent application Ser. No. 60/496,858 filed Aug. 20, 2003, the teaching of which is hereby incorporated by reference for all purposes.

BACKGROUND OF THE INVENTION

Cysteine proteases represent an enzymatic class of proteins that catalyze the hydrolysis of peptide bonds by a nucleophilic sulfhydryl group of a cysteine residue in the active site of the enzyme. Several normal and disease processes in mammals have been associated with cysteine protease activity and include, but are not limited to: osteoporosis, osteoarthritis (Inui, T., O. Ishibashi, et al. *J Biol Chem* 1997, 272(13), 8109-12; Saftig, P., E. Hunziker, et al. *Adv Exp Med Biol* 2000+ADs 2000, 477, 293-303; Saftig, P., E. Hunziker, et al. *Proc Natl Acad Sci U S A* 1998, 95(23), 13453-8), periodontal diseases, Paget's disease, atherosclerosis (Jormsjo, S., D. M. Wuttge, et al. *Am J Pathol* 2002 161(3), 939-45), multiple sclerosis (Beck, H., G. Schwarz, et al. *Eur J Immunol* 2001, 31(12), 3726-36), rheumatoid arthritis (Nakagawa, T. Y., W. H. Brissette, et al. *Immunity* 1999, 10(2), 207-17; Hou, W. S., Z. Li, et al. *Am J Pathol* 2001, 159(6), 2167-77), juvenile onset diabetes, lupus, asthma (Cimerman, N., P. M. Brguljan, et al. *Pflugers Arch* 2001, 442(6 Suppl 1), R204-6), tissue rejection, Alzheimer's disease (Lemere, C. A., J. S. Munger, et al. *Am J Pathol* 1995, 146(4), 848-60), Parkinson's disease (Liu, Y., L. Fallon, et al. *Cell* 2002, 111(2), 209-18), neuronal degeneration, shock (Jaeschke, H., M. A. Fisher, et al. *J Immunol* 1998, 160(7), 3480-6), cancer (Fernandez, P. L., X. Farre, et al. *Int J Cancer* 2001, 95(1), 51-5), malaria (Malhotra, P., P. V. Dasaradhi, et al. *Mol Microbiol* 2002, 45(5), 1245-54), Chagas (Eakin, A. E., A. A. Mills, et al. *J Biol Chem* 1992, 267(11), 7411-20), leishmaniasis, shistosomiasis, and African trypanosomiasis (Caffrey, C. R., S. Scory, et al. *Curr Drug Targets* 2000, 1(2), 155-62; Lalmanach, G., A. Boulange, et al. *Biol Chem* 2002, 383(5), 739-49).

Cathepsins are a subclass of cysteine protease that belong to the enzyme classification EC 3.4.22 (Barrett, A. J., N. D. Rawlings, et al. *Handbook of proteolytic enzymes*. London, Academic Press). Cathepsins play a major role in lysosomal, endosomal, and extracellular protein degradation and have thus been implicated in many disease processes. For example, Cathepsin B [EC 3.4.22.1] has been postulated to play a role in tumor metastasis (Berquin, I. M. and B. F. Sloane *Adv Exp Med Biol* 1996, 389, 281-94).

Cathepsin S [EC 3.4.22.27] is largely expressed in professional antigen presenting cells such as macrophages and dendritic cells. Cathepsin S has been shown to be required for proper MHC class II antigen presentation (Shi, G. P., J. A. Villadangos, et al. *Immunity* 1999, 10(2) 197-206). As a result of its non-redundant role in MHC class II antigen presentation, cathepsin S has been associated with inflammation, arthritis, and atherosclerosis. The selective expression of cathepsin K [EC 3.4.22.38] in osteoclasts coupled with the ability of cathepsin K to degrade type I collagen suggests that it plays a role in normal and pathogenic bone remodeling (Bromme, D., K. Okamoto, et al. *J Biol Chem* 1996, 271(4), 2126-32). There is a need in the art for compounds and methods that selectively inhibit specific cysteine proteases for treating several pathogenic disorders in mammals. The present invention satisfies these and other needs.

SUMMARY OF THE INVENTION

The present invention provides compounds, compositions and methods for the selective inhibition of cathepsin S. The compounds of the present invention are selective for cathepsin S in the presence of other cathepsin isozymes. In a preferred embodiment, the compounds of the present invention are selective for cathepsin S in the presence of cathepsin K, L, B, or combinations thereof. The present invention also provides methods for treating a disease state in a subject by selectively inhibiting cathepsin S in the presence of other cathepsin isozymes. In a preferred aspect, cathepsin S is selectively inhibited in the presence of cathepsin K, L, B, or combinations thereof.

In one aspect, the present invention provides a compound of Formula I:

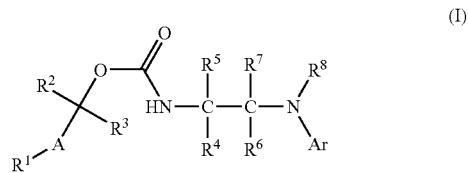

or a pharmaceutically acceptable salt or prodrug thereof, wherein:

A is a member selected from the group consisting of —CH$_2$—, —O—CH$_2$—, —NR$^9$CH$_2$—, —CH$_2$CH$_2$— and a bond;

R$^1$ is a member selected from the group consisting of C$_6$-C$_{10}$ aryl substituted with 0-3 R$^{1a}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 R$^{1a}$, and a C$_3$-C$_8$ heterocycle containing 1 to 2 heteroatoms each independently a member selected from the group consisting of N, O and S, wherein said heterocycle is substituted with 0-2 R$^{1a}$;

each R$^{1a}$ is independently a member selected from the group consisting of F, Cl, Br, CN, NO$_2$, OH, acetyl, C(=O)OR$^{10}$, C(=O)NR$^{10}$R$^{11}$, S(=O)$_2$NR$^{10}$R$^{11}$; C$_3$-C$_7$ cycloalkyl; —SCH$_3$, —S(=O)CH$_3$, —S(=O)$_2$CH$_3$, NR$^{12}$R$^{13}$, C$_1$-C$_6$ alkoxy, C$_1$-C$_3$ perfluoroalkyl, C$_1$-C$_3$ perfluoroalkoxy, a C$_1$-C$_6$ alkyl, phenyl substituted with 0-3 R$^{14}$, a 5- to 6-membered heteroaryl containing 1 to 4 heteroatoms each independently a member selected from the group consisting of N, O and S, wherein said heteroaryl is substituted with 0-3 R$^{14}$, a C$_3$-C$_8$ heterocycle containing 1 to 2 heteroatoms each independently a member selected from the group consisting of N, O and S, wherein said heterocycle is substituted with 0-2 R$^{14}$ and is saturated or partially unsaturated;

R$^2$ is a member selected from the group consisting of a C$_1$-C$_6$ alkyl substituted with 0-2 R$^{2a}$, wherein said C$_1$-C$_6$ alkyl may optionally contain a heteroatom selected from the group consisting of —O—, —S—, —S(=O)— and —S(=O)$_2$—, a C$_2$-C$_6$ alkenyl substituted with 0-1 R$^{2a}$, a C$_3$-C$_6$ alkynyl substituted with 0-1 R$^{2a}$, a C$_3$-C$_7$ cycloalkyl substituted with 0-2 R$^{2b}$, a C$_7$-C$_{11}$ bicycloalkyl substituted with 0-2 $R^{2b}$, phenyl substituted with 0-3 $R^{14}$, a 5- to 6-membered heteroaryl containing 1 to 4 heteroatoms each independently a member selected from the group consisting of N, O and S, wherein said heteroaryl is substituted with 0-3 $R^{14}$;

each $R^{2a}$ is independently a member selected from the group consisting of a $C_6$-$C_{10}$ aryl substituted with 0-3 $R^{14}$, a perfluorophenyl, a $C_3$-$C_8$ cycloalkyl substituted with 0-2 $R^{2b}$, a $C_7$-$C_{11}$ bicycloalkyl substituted with 0-2 $R^{2b}$, and a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{14}$;

each $R^{2b}$ is independently a member selected from the group consisting of H, OH, F, Cl, $C_1$-$C_6$ alkyl, $C_1$-$C_6$ alkoxy, $CF_3$, and $OCF_3$;

$R^3$ is a member selected from the group consisting of H and $C_1$-$C_6$ alkyl;

$R^4$ is a member selected from the group consisting of H, $C(=O)OR^{15}$, $C(=O)NR^{16}R^{17}$, phenyl substituted with 0-2 $R^{14}$, 5- to 6-membered heteroaryl containing 1 to 4 heteroatoms each independently a member selected from the group consisting of N, O and S, wherein said heteroaryl is substituted with 0-2 $R^{14}$, $C_3$-$C_7$ cycloalkyl, $C_1$-$C_6$ alkyl substituted with 0-2 $R^{20}$, wherein said $C_1$-$C_6$ alkyl may optionally contain a heteroatom selected from the group consisting of —O—, —S—, —S(=O)—, —S(=O)$_2$— and —NR$^{16}$—;

each of $R^5$, $R^6$, $R^7$ and $R^8$ is independently a member selected from the group consisting of H and $C_1$-$C_6$ alkyl; alternatively, $R^4$ and $R^6$ are taken together to form a $C_5$-$C_7$ cycloalkyl;

each $R^9$ is independently a member selected from the group consisting of H and $C_1$-$C_4$ alkyl;

each of $R^{10}$ and $R^{11}$ is independently a member selected from the group consisting of H, and $C_1$-$C_4$ alkyl;

alternatively, $R^{10}$ and $R^{11}$ on the same nitrogen are taken together to form a 5- to 7-membered heterocyclic ring containing 1-2 heteroatoms each independently a member selected from the group consisting of N, O and S;

each $R^{12}$ is independently a member selected from the group consisting of H, $C_1$-$C_4$ alkyl, ($C_1$-$C_4$ alkyl)-$C(=O)$— and ($C_1$-$C_4$ alkyl)-$S(=O)_2$—;

each $R^{13}$ is independently a member selected from the group consisting of H and $C_1$-$C_4$ alkyl;

alternatively, $R^{12}$ and $R^{13}$ on the same nitrogen are taken together to form a 5- to 7-membered heterocyclic ring containing 1-2 heteroatoms each independently a member selected from the group consisting of N, O and S;

each $R^{14}$ is independently a member selected from the group consisting of H, OH, F, Cl, Br, CN, $NO_2$, $COOR^{10}$, $C(=O)NR^{10}R^{11}$, $S(=O)_2NR^{10}R^{11}$, acetyl, —$SCH_3$, —$S(=O)CH_3$, —$S(=O)_2CH_3$, $NR^{12}R^{13}$, $C_1$-$C_6$ alkoxy, $C_1$-$C_3$ perfluoroalkyl, $C_1$-$C_3$ perfluoroalkoxy, and a $C_1$-$C_6$ alkyl;

each $R^{15}$ is independently a member selected from the group consisting of H, $C_3$-$C_7$ cycloalkyl, $C_1$-$C_4$ alkyl substituted with 0-1 $R^{18}$, and a phenyl substituted with 0-3 $R^{14}$;

each $R^{16}$ is independently a member selected from the group consisting of H, $C_3$-$C_8$ cycloalkyl, a phenyl substituted with 0-3 $R^{14}$, and a $C_1$-$C_6$ alkyl substituted with 0-1 $R^{18}$;

each $R^{17}$ is independently a member selected from the group consisting of H and $C_1$-$C_4$ alkyl;

alternatively, $R^{16}$ and $R^{17}$ on the same N atom are taken together to form a $C_5$-$C_7$ heterocycle containing 1-2 heteroatoms each independently a member selected from the group consisting of N, O and S.

each $R^{18}$ is independently a member selected from the group consisting of H, $C_3$-$C_7$ cycloalkyl, a phenyl substituted with 0-3 $R^{14}$ and a 5- to 6-membered heteroaryl containing 1 to 4 heteroatoms each independently a member selected from the group consisting of N, O and S, wherein said 5- to 6-membered heteroaryl is substituted with 0-3 $R^{14}$;

Ar is a member selected from the group consisting of phenyl substituted with 0-3 $R^{19}$, and 5- to 6-membered heteroaryl containing 1 to 4 heteroatoms each independently a member selected from the group consisting of N, O and S substituted with 0-3 $R^{19}$;

each $R^{19}$ is independently a member selected from the group consisting of H, F, Cl, Br, CN, $OR^{21}$, $SCH_3$, $S(=O)CH_3$, $S(=O)_2CH_3$, $S(=O)_2NR^{10}R^{11}$, $NR^{12}R^{13}$, acetyl, $C(=O)NR^{10}R^{11}$, $CO_2R^{10}$, $C(=NH)NH_2$, $C_1$-$C_6$ alkyl, $CF_3$; and a 5- to 6-membered heteroaryl containing 1 to 4 heteroatoms each independently a member selected from the group consisting of N, O and S, wherein said heteroaryl is substituted with 0-3 $R^{14}$;

alternatively, $R^{19}$ and $R^8$ are taken together to form a 5- to 7-membered heterocyclic ring containing 1-2 heteroatoms, each independently a member selected from the group consisting of N, O and S, wherein said 5 to 7 membered heterocyclic ring is ortho-fused to Ar and wherein said 5- to 7-membered heterocyclic ring may be optionally substituted with 0-2 $R^{22}$;

each $R^{20}$ is independently a member selected from the group consisting of H, OH, F, Cl, CN, $NO_2$, $C(=O)OR^{15}$, $C(=O)NR^{16}R^{17}$, $NR^{12}R^{13}$, $C_1$-$C_3$ perfluoroalkoxy, $C_1$-$C_3$ perfluoroalkyl, $C_1$-$C_4$ alkoxy, $C_2$-$C_4$ alkenyl, $C_2$-$C_4$ alkynyl, phenyl substituted with 0-3 $R^{14}$, 5- to 6-membered heteroaryl containing 1 to 4 heteroatoms each independently a member selected from the group consisting of N, O and S, wherein said heteroaryl is substituted with 0-3 $R^{14}$, $C_3$-$C_8$ heterocycle containing 1 to 2 heteroatoms each independently a member selected from the group consisting of N, O and S, wherein said heterocycle is substituted with 0-2 $R^{14}$ and is saturated or partially unsaturated, and $C_3$-$C_8$ cycloalkyl;

each $R^{21}$ is independently a member selected from the group consisting of H, $CF_3$, $CHF_2$, $C_1$-$C_6$ alkyl, $C_3$-$C_8$ cycloalkyl, a phenyl substituted with 0-3 $R^{14}$, a 5- to 6-membered heteroaryl containing 1 to 4 heteroatoms each independently a member selected from the group consisting of N, O and S, wherein said 5- to 6-membered heteroaryl is substituted with 0-3 $R^{14}$, and a $CH_2$ substituted with 1 $R^{18}$; and each $R^{22}$ is independently a member selected from the group consisting of $C_1$-$C_4$ alkyl, F, Cl and $C_1$-$C_4$ alkoxy, $CF_3$ and $OCF_3$, or alternatively, two $R^{22}$ may be combined to form $C_3$-$C_6$ cycloalkyl.

In a second aspect, the present invention provides a pharmaceutical composition comprising a compound of Formula I, as described above, and a pharmaceutically acceptable excipient.

In a third aspect, the present invention provides a method of selectively inhibiting the cathepsin S activity in a mammal in need thereof, comprising administering to the mammal a therapeutically effective amount of a compound of Formula I, as described above, or a pharmaceutically acceptable salt or prodrug thereof.

These and other aspects, embodiments and objects will become more apparent when read with the detailed description and figure which follow.

DETAILED DESCRIPTION OF THE INVENTION

I. Definitions

Figure 1:
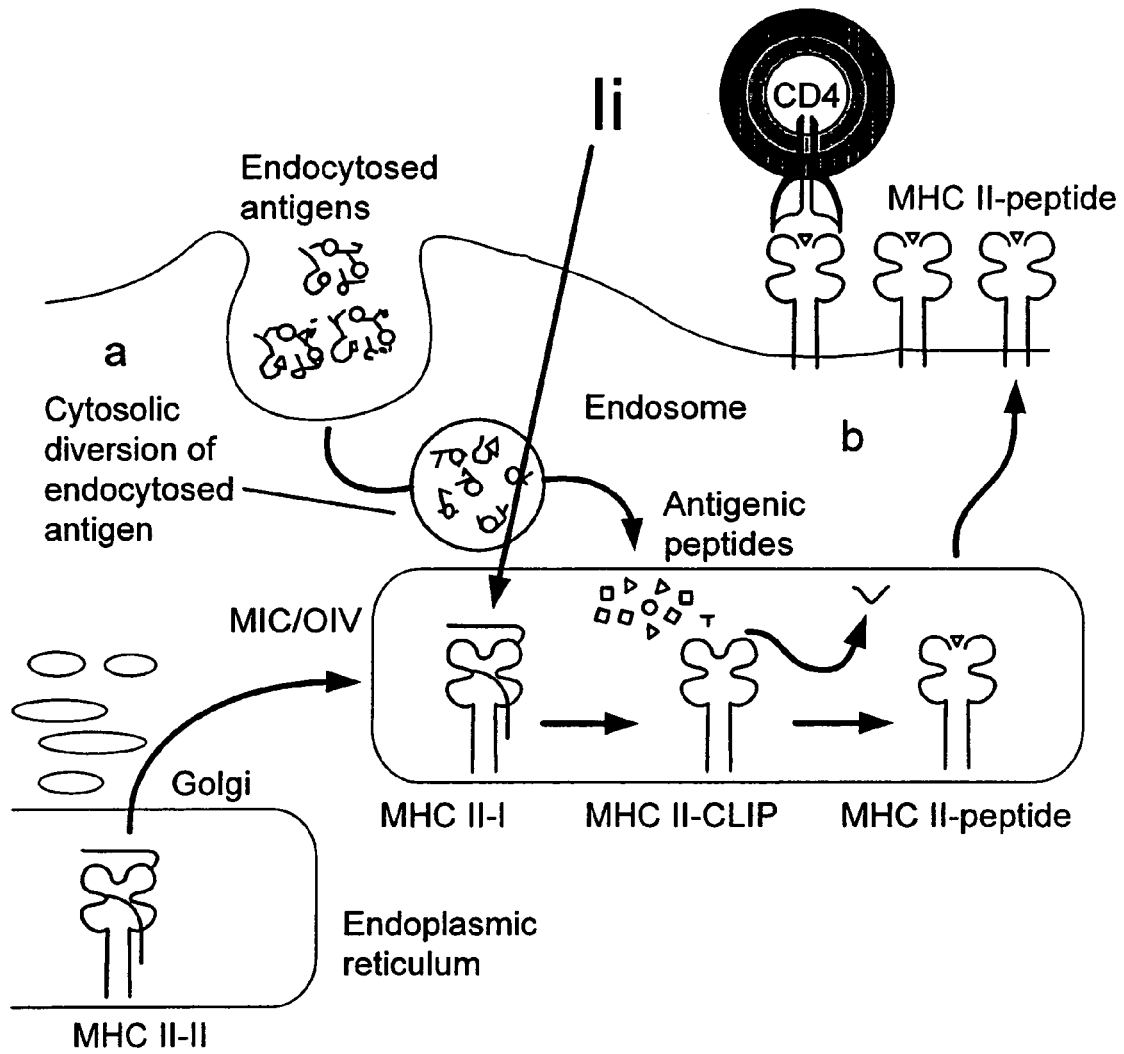
FIG. 1 depicts MHC II antigen presentation.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

As used in this disclosure, the following abbreviations and terms have the defined meaning, unless expressly modified in the context in which the term is used:

| | |
|---|---|
| Ac | acetyl |
| Bn | benzyl |
| Boc | t-butoxycarbonyl |
| Cbz or Z | benzyloxycarbonyl |
| DCC | N,N'-dicyclohexylcarbodiimide |
| DCM | dichoromethane |
| DIC | N,N'-diisopropylcarbodiimide |
| DIBAL | diisobutylaluminum hydride |
| DIEA or DIPEA | diisopropylethylamine |
| DMAP | 4-(dimethylamino)pyridine |
| DMF | dimethylformamide |
| DMSO | dimethyl sulfoxide |
| EDC or EDCI | 1-ethyl-3-(dimethylaminopropyl)-carbodiimide |
| Fmoc | 9-fluorenylmethoxycarbonyl |
| HATU | O-(7-zabenzoatriazol-1-yl)-N,N,N',N'-tetramethyluronium hexafluorophosphate |
| HOBt | 1-hydroxybenzotriazole |
| KHMDS | potassium hexamethyldisilazide |
| LAH | lithium aluminum hydride |
| LDA | lithium diisopropylamide |
| LHMDS | lithium hexamethyldisilazide |
| m-CPBA | m-chloroperbenzoic acid |
| MW | microwave |
| NaHMDS | sodium hexamethyldisilazide |
| PG | protecting group |
| PTSA | p-toluenesulfonic acid |
| Py | pyridine |
| RT or rt | room temperature |
| TEA | triethylamine |
| Tf | trifluoromethanesulfonyl |
| TFA | trifluoroacetic acid |
| THF | tetrahydrofuran |
| Tol | p-tolyl |

The term "lower" referred to above and hereinafter in connection with organic radicals or compounds respectively defines a compound or radical which can be branched or unbranched with up to and including 7, preferably up to and including 4 and (as unbranched) one or two carbon atoms.

The term "perfluoro" referred to above and hereinafter in connection with organic radicals or compounds respectively, defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

An alkyl group is branched or unbranched and contains 1 to 7 carbon atoms, preferably 1-4 carbon atoms. Alkyl represents, for example, methyl, ethyl, propyl, butyl, isopropyl or isobutyl.

Alkenyl represents either straight chain or branched alkenyl of 2 to 7 carbon atoms, preferably 2-4 carbon atoms, e.g. as vinyl, propenyl, isopropenyl, butenyl, isobutenyl or butadienyl.

Alkynyl represents either straight chain or branched alkynyl of 2 to 7 carbon atoms, preferably 2-4 carbon atoms, e.g. as acetylenyl, propynyl, isopropynyl, butynyl or isobutynyl.

Alkyl, alkenyl or alkynyl can be substituted by up to 3 substituents selected from alkoxy, aryl, heterocyclyl, hydroxy, halogen, cyano, optionally substituted amino, optionally substituted amino-oxy, or trifluoromethyl.

Alkylene represents either straight chain or branched alkylene of 1 to 7 carbon atoms, i.e. a divalent hydrocarbon radical of 1 to 7 carbon atoms; for instance, straight chain alkylene being the bivalent radical of formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain monosubstituted by $C_1$-$C_3$-alkyl (preferably methyl) or disubstituted on the same or different carbon atoms by $C_1$-$C_3$-alkyl (preferably methyl), the total number of carbon atoms being up to and including 7.

An alkoxy (or alkyloxy) group preferably contains 1-7 carbon atoms, more preferably 1-6 carbon atoms, and represents for example ethoxy, propoxy, isopropoxy, isobutoxy, preferably methoxy. Alkoxy includes cycloalkyloxy and cycloalkyl-alkyloxy.

Halogen (halo) preferably represents chloro or fluoro, but may also be bromo or iodo.

Aryl represents monocyclic, bicyclic or tricyclic aryl, for example, phenyl or phenyl mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

Benzyl represents a phenyl-$CH_2$— group. Substituted benzyl means a benzyl group in which the phenyl ring is substituted with one or more ring system substituents. Representative benzyl groups include 4-bromobenzyl, 4-methoxybenzyl, 2,4-dimethoxybenzyl, and the like.

Heteroaryl represents monocyclic or bicyclic heteroaryl, for example pyridyl, indolyl, indazolyl, quinoxalinyl, quinolinyl, isoquinolinyl, benzothienyl, benzofuranyl, benzopyranyl, benzothiopyranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2, 4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Biaryl may preferably be, e.g., biphenyl, namely 2, 3 or 4-biphenyl, preferably, 4-biphenyl, each optionally substituted by, e.g., alkyl, alkoxy, halogen, trifluoromethyl or cyano, or heterocyclic-carbocyclic biaryl, preferably, e.g., thienylphenyl, pyrrolylphenyl and pyrazolylphenyl.

Cycloalkyl represents a saturated cyclic hydrocarbon optionally substituted by alkyl which contains 3 to 10 ring carbons and is advantageously cyclopentyl, cyclohexyl, cycloheptyl or cyclooctyl optionally substituted by alkyl.

Amino can be optionally substituted by, e.g., one or two alkyl groups.

Carbocyclic represents a saturated or partially unsaturated cyclic hydrocarbon with 5 to 7 ring members, wherein 1 to 2 ring members can optionally be replaced with one of the following groups: —O—, —S—, —S(=O)—, —S(=O)$_2$— and —NR—, wherein R is a radical of the present invention.

Heterocyclyl represents a saturated cyclic hydrocarbon containing one or more, preferably 1 or 2, hetero atoms selected from O, N or S, and from 3 to 10, preferably 5 to 8, ring atoms; for example, tetrahydrofuranyl, tetrahydrothienyl, tetrahydropyrrolyl, piperidinyl, piperazinyl or morpholino; all of which can be optionally substituted, for instance as hereinbefore defined for aryl.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

"Treat", "treating" and "treatment" refer to a method of alleviating or abating a disease and/or its attendant symptoms.

"Inhibition", "inhibits" and "inhibitor" refer to a compound that prohibits, or a method of prohibiting, a specific action or function.

"Inhibition constant", $K_i$, is the dissociation constant of the enzyme-inhibitor complex, or the reciprocal of the binding affinity of the inhibitor to the enzyme. For classical inhibition the value of $K_i$ is much greater than the enzyme concentration and the $K_i$ can be measured by monitoring the rate of reaction for a competitive substrate at multiple inhibitor concentrations. The inhibited rates are then fit by nonlinear regression to the following equation:

$$v_i/v_o = \frac{K_m + [S]}{K_m(1 + [I]/K_i) + [S]}$$

where $v_o$ is the initial rate of substrate processing in the absence of inhibitor, $v_i$ is the initial rate of substrate processing at a concentration [I] of inhibitor, $K_m$ is the steady state Michaelis constant (Fersht, A. *Structure and Mechanism in Protein Science*. New York, W. H. Freeman and Company, 1999), and [S] is the concentration of competitive substrate.

The assumption being made for the classical inhibition described above is that the free inhibitor concentration is equal to the total inhibitor concentration. For inhibitors that have $K_i$'s that are approximately equal to the enzyme concentration [E], the assumption that the free inhibitor concentration is equal to the total inhibitor concentration is no longer valid and an alternative equation has to be fit for determination of the apparent inhibition constant, $K_i^{app}$ using described methods (Kuzmic, P., K. C. Elrod, et al. *Anal Biochem* 2000, 286(1), 45-50):

$$v_i/v_o = \frac{[E] - [I] - K_i^{app} + SQRT(([E] - [I] - K_i^{app})^2 + 4[E]K_i^{app})}{2[E]}.$$

The inhibition constant, $K_i$, can be determined from the apparent inhibition constant, $K_i^{app}$, for competitive inhibitors by using the following relationship:

$$K_i = \frac{K_i^{app}}{1 + [S]/K_m}.$$

Polycyclic ring systems in which any two adjacent rings have two (e.g., only two), adjacent atoms in common are said to be "ortho-fused". Such ring systems have n common sides and 2n common atoms.

"Therapeutically effective amount" refers to that amount of the compound being administered sufficient to prevent development of or alleviate to some extent one or more of the symptoms of the condition or disorder being treated.

"Composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the Formulation and deleterious to the recipient thereof.

"Subject" refers to animals such as mammals, including, but not limited to, primates (e.g., humans), cows, sheep, goats, horses, dogs, cats, rabbits, rats, mice and the like. In certain aspects, the subject is a human.

II. General

Cathepsin S is a cysteine protease that has been associated with several normal and disease processes in mammals.

Specifically, cathepsin S has been directly associated with inflammation, arthritis, and atherosclerosis, as a result of its role in MHC class II antigen presentation. In a preferred aspect, the present invention provides compounds that inhibit the activity of cathepsin S. The present invention also provides methods for treating several disease states in mammals by inhibiting the activity of cathepsin S. In a more preferred aspect, the compounds of the present invention selectively inhibit cathepsin S in the presence of at least one cathepsin isozyme.

III. Compounds

A. Preparation of Compounds

In the following schemes, several methods of preparing the compounds of the present invention are illustrative. One of skill in the art will appreciate that these methods are representative, and in no way inclusive of all methods for preparing the compounds of the present invention. The radicals in schemes 1-4 are as described in Formula I.

In certain aspects, one route to compounds provided by the present invention is shown in Scheme 1.

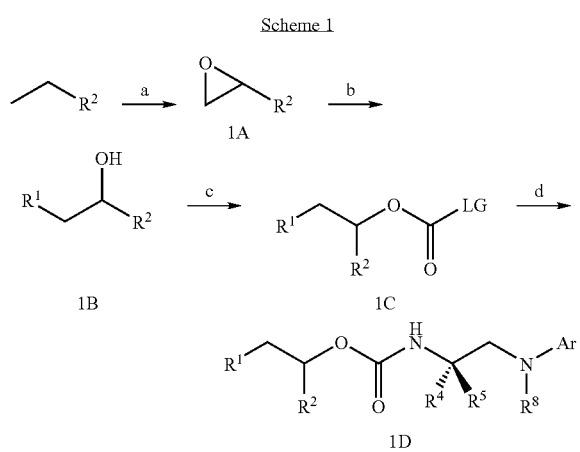

a) MeReO$_3$, H$_2$O$_2$, 3-cyanopyridine, CH$_2$Cl$_2$;
b) Heterocycle R$^1$H, K$_2$CO$_3$, DMF, 160° C., microwave, 6 min;
or aliphatic amine neat, microwave irradiation
c) 4-Nitrophenyl chloroformate, pyridine, heat or 4-nitrophenyl chloroformate, DMAP, DMF, heat;
d) NH$_2$-CR$^4$R$^5$CH$_2$NR$^8$Ar, DMF, DIEA.

In this reaction, a terminal olefin was oxidized to the corresponding racemic terminal epoxide 1A using the methyltrioxorhenium method (Sharpless, K. B. et al. A simple and efficient method for epoxidation of terminal alkenes. *Chem. Commun.* 1997, 1565; Sharpless, K. B. et al. Highly efficient epoxidation of olefins using aqueous H$_2$O$_2$ and catalytic methyltrioxorhenium/pyridine: Pyridine-mediated ligand acceleration *J. Am. Chem. Soc.* 1997, 119, 6189.) This intermediate (which is commercially available for certain R$^2$ substituents) was then opened to 1B. If R$^1$H is an NH containing heterocycle, the reaction was effectuated using powdered potassium carbonate in DMF and microwave irradiation. If R$^1$H is an aliphatic amine, the reaction was effectuated in neat amine using microwave irradiation. The hydroxyl of 1B was then functionalized as a mixed carbonate 1C with a leaving group (LG). This was done with 4-nitrophenyl carbonate in pyridine or in DMF with DMAP as base. If these conditions were not tolerated, then the transformation was affected with phosgene in CH$_2$Cl$_2$. Other leaving groups (LG) can also be employed: methods for preparing compounds 1C wherein LG represents Cl are known in the art and may be used instead as those of skill in the art will recognize. Finally, the mixed carbonate 1C was reacted with an amine NH$_2$-CR$^4$R$^5$CH$_2$NR$^8$Ar in DMF using DIEA as base to afford the desired carbamate 1D.

Another route to compounds described in this invention is shown in Scheme 2.

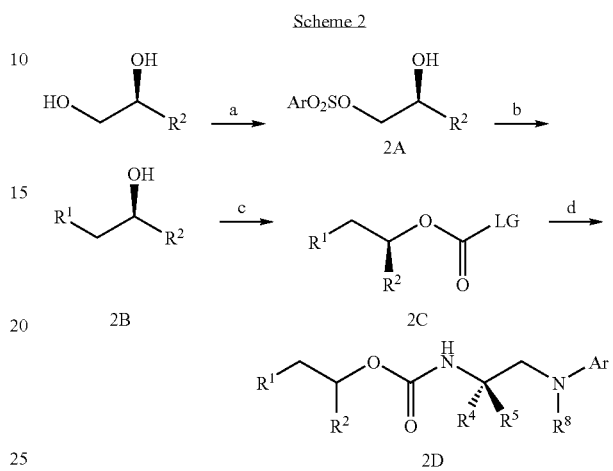

a) ArSO$_2$Cl, pyridine, CH$_2$Cl$_2$;
b) Heterocycle R$^1$H, K$_2$CO$_3$, DMF, 160° C., microwave, 6 min or amine, neat, 160° C., microwave, 6 min;
c) 4-Nitrophenyl chloroformate, pyridine, heat or 4-nitrophenyl chloroformate, DMAP, DMF, heat or phosgene, CH$_2$Cl$_2$, RT;
d) NH$_2$-CR$^4$R$^5$CH$_2$NR$^8$Ar, DMF, DIEA Starting with a diol (available either through dihydroxylation of terminal olefins or reduction of the appropriate lactic acid), the primary hydroxyl group is selectively sulfonylated to generate 2A. The terminal carbon is then functionalized using for example, either a heterocyclic anion or an organic amine to afford 2B. The secondary alcohol is then activated for carbamate formation using either nitrophenyl chloroformate or phosgene to afford 2C. As above, other reactive acylating agents such as chloroformates (2C, where LG=Cl) may also be generated by known methods. This intermediate is then reacted with an amine to furnish the desired 2D. For the preparation and derivatization of optically pure diols, see Sharpless, K. B. et al. Catalytic asymmetric dihydroxylation *Chem. Rev.* 1994, 94, 2483; Sharpless, K. B. et al. In *Catalytic Asymmetric Synthesis* Ojima, I. (Ed.); Wiley-VCH, 2002; 2$^{nd}$ Ed. pp. 357-398.

The arylaminoethylamines 3A (Scheme 3) used in the present invention can be prepared by a decarboxylative ring opening of oxazolidin-2-one with an aromatic amine as described in E. Altman et al. *J. Med Chem.* 2002, 45, 2352-54 and references cited therein.

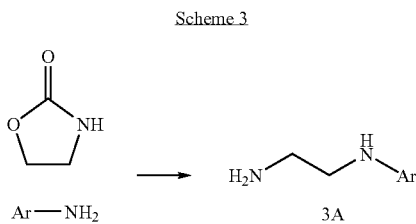

Another synthetic route to the diamines used in the present invention is described in Scheme 4.

Scheme 4

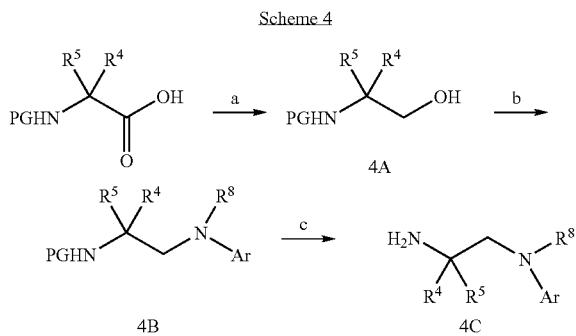

a) [BH$_3$·THF, THF 0° C.] or [i)TEA, i-butyl-chloroformate, THF, 0° C.; ii) NaBH$_4$, H$_2$O, 0° C. to RT];
b) i) Dess-Martin periodinane, DCM; ii) NHR$^8$Ar, NaC-NBH$_3$, AcOH, MeOH;
c) removal of PG.

A N-protected amino acid can be reduced using either the BH$_3$ method or NaBH$_4$ reduction of the corresponding mixed anhydride [see R. C. Larock *A guide to functional group preparations* pp. 548-552, Wiley-VCH, 1989] to obtain 4A (Scheme 4). One can then oxidize the alcohol to the aldehyde and reductively aminate the resulting aldehyde with an amine to afford 4B. This intermediate can then be deprotected using the appropriate reagents for the PG, such as TFA for Boc.

Synthetic approaches to indolines used in this invention are widely describe in the literature and well know to one skilled in the art. The typical methods are illustrated, but are not limited to, in the following references. See: (a) G. W. Gribble et al. *Synthesis* 1977, 859; (b) A. Smith et al. *Chem. Commun.* 1965, 427; (c) G. W. Gribble et al. *J. Am. Chem. Soc.* 1974, 96, 7812; (d) J. G. Berger *Synthesis* 1974, 508; (e) L. J. Dolby et al. *J. Heterocycl. Chem.* 1966, 3, 124; (f) W. A. Remers et al. *J. Org. Chem.* 1971, 36, 279; (g) S. O'Brien et al. *J. Chem. Soc.* 1960, 4609; (h) Y. Kikugawa et al. *Synthesis* 1978, 477.

B. Preferred Compounds

In one aspect, the present invention provides a compound of Formula I:

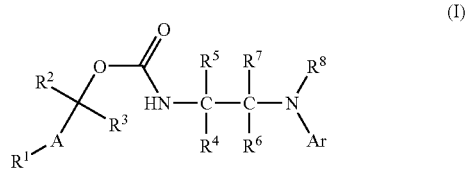

(I)

or a pharmaceutically acceptable salt or prodrug thereof, wherein:

A is a member selected from the group consisting of —CH$_2$—, —O—CH$_2$—, —NR$^9$CH$_2$—, —CH$_2$CH$_2$— and a bond;

R$^1$ is a member selected from the group consisting of C$_6$-C$_{10}$ aryl substituted with 0-3 R$^{1a}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 R$^{1a}$, and a C$_3$-C$_8$ heterocycle containing 1 to 2 heteroatoms each independently a member selected from the group consisting of N, O and S, wherein said heterocycle is substituted with 0-2 R$^{1a}$;

each R$^{1a}$ is independently a member selected from the group consisting of F, Cl, Br, CN, NO$_2$, OH, acetyl, C(=O)OR$^{10}$, C(=O)NR$^{10}$R$^{11}$, S(=O)$_2$NR$^{10}$R$^{11}$; C$_3$-C$_7$ cycloalkyl; —SCH$_3$, —S(=O)CH$_3$, —S(=O)$_2$CH$_3$, NR$^{12}$R$^{13}$, C$_1$-C$_6$ alkoxy, C$_1$-C$_3$ perfluoroalkyl, C$_1$-C$_3$ perfluoroalkoxy, a C$_1$-C$_6$ alkyl, phenyl substituted with 0-3 R$^{14}$, a 5- to 6-membered heteroaryl containing 1 to 4 heteroatoms each independently a member selected from the group consisting of N, O and S, wherein said heteroaryl is substituted with 0-3 R$^{14}$, a C$_3$-C$_8$ heterocycle containing 1 to 2 heteroatoms each independently a member selected from the group consisting of N, O and S, wherein said heterocycle is substituted with 0-2 R$^{14}$ and is saturated or partially unsaturated;

R$^2$ is a member selected from the group consisting of a C$_1$-C$_6$ alkyl substituted with 0-2 R$^{2a}$, wherein said C$_1$-C$_6$ alkyl may optionally contain a heteroatom selected from the group consisting of —O—, —S—, —S(=O)— and —S(=O)$_2$—, a C$_2$-C$_6$ alkenyl substituted with 0-1 R$^{2a}$, a C$_3$-C$_6$ alkynyl substituted with 0-1 R$^{2a}$, a C$_3$-C$_7$ cycloalkyl substituted with 0-2 R$^{2b}$, a C$_7$-C$_{11}$ bicycloalkyl substituted with 0-2 R$^{2b}$, phenyl substituted with 0-3 R$^{14}$, a 5- to 6-membered heteroaryl containing 1 to 4 heteroatoms each independently a member selected from the group consisting of N, O and S, wherein said heteroaryl is substituted with 0-3 R$^{14}$;

each R$^{2a}$ is independently a member selected from the group consisting of a C$_6$-C$_{10}$ aryl substituted with 0-3 R$^{14}$, a perfluorophenyl, a C$_3$-C$_8$ cycloalkyl substituted with 0-2 R$^{2b}$, a C$_7$-C$_{11}$ bicycloalkyl substituted with 0-2 R$^{2b}$, and a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 R$^{14}$;

each R$^{2b}$ is independently a member selected from the group consisting of H, OH, F, Cl, C$_1$-C$_6$ alkyl, C$_1$-C$_6$ alkoxy, CF$_3$, and OCF$_3$;

R$^3$ is a member selected from the group consisting of H and C$_1$-C$_6$ alkyl;

R$^4$ is a member selected from the group consisting of H, C(=O)OR$^{15}$, C(=O)NR$^{16}$R$^{17}$, phenyl substituted with 0-2 R$^{14}$, 5- to 6-membered heteroaryl containing 1 to 4 heteroatoms each independently a member selected from the group consisting of N, O and S, wherein said heteroaryl is substituted with 0-2 R$^{14}$, C$_3$-C$_7$ cycloalkyl, C$_1$-C$_6$ alkyl substituted with 0-2 R$^{20}$, wherein said C$_1$-C$_6$ alkyl may optionally contain a heteroatom selected from the group consisting of —O—, —S—, —S(=O)—, —S(=O)$_2$— and —NR$^{16}$—;

each of R$^5$, R$^6$, R$^7$ and R$^8$ is independently a member selected from the group consisting of H and C$_1$-C$_6$ alkyl;

alternatively, R$^4$ and R$^6$ are taken together to form a C$_5$-C$_7$ cycloalkyl;

each R$^9$ is independently a member selected from the group consisting of H and C$_1$-C$_4$ alkyl;

each of R$^{10}$ and R$^{11}$ is independently a member selected from the group consisting of H, and C$_1$-C$_4$ alkyl;

alternatively, R$^{10}$ and R$^{11}$ on the same nitrogen are taken together to form a 5- to 7-membered heterocyclic ring containing 1-2 heteroatoms each independently a member selected from the group consisting of N, O and S;

each $R^{12}$ is independently a member selected from the group consisting of H, $C_1$-$C_4$ alkyl, ($C_1$-$C_4$ alkyl)—C(=O)— and ($C_1$-$C_4$ alkyl)-S(=O)$_2$—;

each $R^{13}$ is independently a member selected from the group consisting of H and $C_1$-$C_4$ alkyl;

alternatively, $R^{12}$ and $R^{13}$ on the same nitrogen are taken together to form a 5- to 7-membered heterocyclic ring containing 1-2 heteroatoms each independently a member selected from the group consisting of N, O and S;

each $R^{14}$ is independently a member selected from the group consisting of H, OH, F, Cl, Br, CN, NO$_2$, COOR$^{10}$, C(=O)NR$^{10}$R$^{11}$, S(=O)$_2$NR$^{10}$R$^{11}$, acetyl, —SCH$_3$, —S(=O)CH$_3$, —S(=O)$_2$CH$_3$, NR$^{12}$R$^{13}$, $C_1$-$C_6$ alkoxy, $C_1$-$C_3$ perfluoroalkyl, perfluoroalkoxy, and a $C_1$-$C_6$ alkyl;

each $R^{15}$ is independently a member selected from the group consisting of H, $C_3$-$C_7$ cycloalkyl, $C_1$-$C_4$ alkyl substituted with 0-1 $R^{18}$, and a phenyl substituted with 0-3 $R^{14}$;

each $R^{16}$ is independently a member selected from the group consisting of H, $C_3$-$C_8$ cycloalkyl, a phenyl substituted with 0-3 $R^{14}$, and a $C_1$-$C_6$ alkyl substituted with 0-1 $R^{18}$;

each $R^{17}$ is independently a member selected from the group consisting of H and $C_1$-$C_4$ alkyl; alternatively, $R^{16}$ and $R^{17}$ on the same N atom are taken together to form a $C_5$-$C_7$ heterocycle containing 1-2 heteroatoms each independently a member selected from the group consisting of N, O and S.

each $R^{18}$ is independently a member selected from the group consisting of H, $C_3$-$C_7$ cycloalkyl, a phenyl substituted with 0-3 $R^{14}$ and a 5- to 6-membered heteroaryl containing 1 to 4 heteroatoms each independently a member selected from the group consisting of N, O and S, wherein said 5- to 6-membered heteroaryl is substituted with 0-3 $R^{14}$;

Ar is a member selected from the group consisting of phenyl substituted with 0-3 $R^{19}$, and 5- to 6-membered heteroaryl containing 1 to 4 heteroatoms each independently a member selected from the group consisting of N, O and S substituted with 0-3 $R^{19}$;

each $R^{19}$ is independently a member selected from the group consisting of H, F, Cl, Br, CN, OR$^{21}$, SCH$_3$, S(=O)CH$_3$, S(=O)$_2$CH$_3$, S(=O)$_2$NR$^{10}$R$^{11}$, NR$^{12}$R$^{13}$, acetyl, C(=O)NR$^{10}$R$^{11}$, CO$_2$R$^{10}$, C(=NH)NH$_2$, $C_1$-$C_6$ alkyl, CF$_3$; and a 5- to 6-membered heteroaryl containing 1 to 4 heteroatoms each independently a member selected from the group consisting of N, O and S, wherein said heteroaryl is substituted with 0-3 $R^{14}$;

alternatively, $R^{19}$ and $R^8$ are taken together to form a 5- to 7-membered heterocyclic ring containing 1-2 heteroatoms, each independently a member selected from the group consisting of N, O and S, wherein said 5 to 7 membered heterocyclic ring is ortho-fused to Ar and wherein said 5- to 7-membered heterocyclic ring may be optionally substituted with 0-2 $R^{22}$;

each $R^{20}$ is independently a member selected from the group consisting of H, OH, F, Cl, CN, NO$_2$, C(=O)OR$^{15}$, C(=O)NR$^{16}$R$^{17}$, NR$^{12}$R$^{13}$, $C_1$-$C_3$ perfluoroalkoxy, $C_1$-$C_3$ perfluoroalkyl, $C_1$-$C_4$ alkoxy, $C_2$-$C_4$ alkenyl, $C_2$-$C_4$ alkynyl, phenyl substituted with 0-3 $R^{14}$, 5- to 6-membered heteroaryl containing 1 to 4 heteroatoms each independently a member selected from the group consisting of N, O and S, wherein said heteroaryl is substituted with 0-3 $R^{14}$, $C_3$-$C_8$ heterocycle containing 1 to 2 heteroatoms each independently a member selected from the group consisting of N, O and S, wherein said heterocycle is substituted with 0-2 $R^{14}$ and is saturated or partially unsaturated, and $C_3$-$C_8$ cycloalkyl;

each $R^{21}$ is independently a member selected from the group consisting of H, CF$_3$, CHF$_2$, $C_1$-$C_6$ alkyl, $C_3$-$C_8$ cycloalkyl, a phenyl substituted with 0-3 $R^{14}$, a 5- to 6-membered heteroaryl containing 1 to 4 heteroatoms each independently a member selected from the group consisting of N, O and S, wherein said 5- to 6-membered heteroaryl is substituted with 0-3 $R^{14}$, and a CH$_2$ substituted with 1 $R^{18}$; and each $R^{22}$ is independently a member selected from the group consisting of $C_1$-$C_4$ alkyl, F, Cl and $C_1$-$C_4$ alkoxy, CF$_3$ and OCF$_3$, or alternatively, two $R^{22}$ may be combined to form $C_3$-$C_6$ cycloalkyl.

Compounds of the present invention are cathepsin S inhibitors. In particularly preferred aspects, the cathepsin S inhibitors are non-inhibitory toward cathepsin K, L, B, or combinations thereof.

In a preferred aspect, the present invention provides a compound according to Formula Ia:

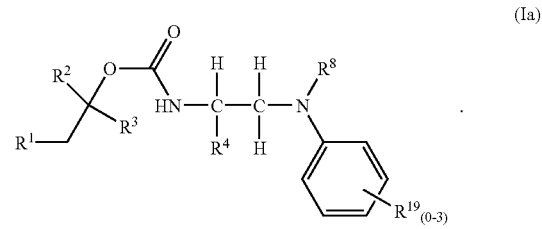

(Ia)

wherein $R^3$ is H.

In certain aspects, compounds of Formula Ia wherein:

$R^2$ is a member selected from the group consisting of a $C_1$-$C_6$ alkyl substituted with 0-1 $R^{2a}$, a $C_3$-$C_7$ cycloalkyl substituted with 0-2 $R^{2b}$, a $C_7$-$C_{11}$ bicycloalkyl substituted with 0-2 $R^{2b}$, and phenyl substituted with 0-3 $R^{14}$; and each $R^{2a}$ is independently a member selected from the group consisting of a $C_6$-$C_{10}$ aryl substituted with 0-3 $R^{14}$, a $C_3$-$C_8$ cycloalkyl substituted with 0-2 $R^{2b}$, and a $C_7$-$C_{11}$ bicycloalkyl substituted with 0-2 $R^{2b}$ are especially preferred.

In certain other aspects, compounds of Formula Ia wherein:

$R^2$ is selected from the group consisting of $C_1$-$C_6$ alkyl, and $C_1$-$C_4$ alkyl substituted with 1 $R^{2a}$; and $R^{2a}$ is selected from the group consisting of $C_3$-$C_7$ cycloalkyl substituted with 0-2 $R^{2b}$, and a $C_7$-$C_{11}$ bicycloalkyl substituted with 0-2 $R^{2b}$ are also preferred.

In yet other aspects, compounds of Formula Ia wherein:

$R^1$ is a member selected from the group consisting of a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1a}$, and a $C_3$-$C_8$ heterocycle containing 1 to 2 heteroatoms each independently a member selected from the group consisting of N, O and S, wherein said heterocycle is substituted with 0-2 $R^{1a}$ are preferred.

$R^1$ is preferably a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1a}$. Suitable $R^1$ groups of this formula include the following:

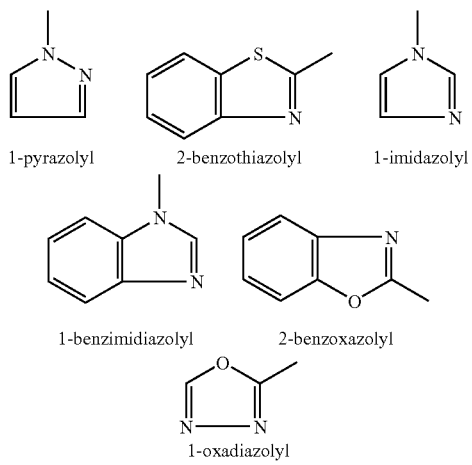

1-pyrazolyl    2-benzothiazolyl    1-imidazolyl 1-benzimidiazolyl    2-benzoxazolyl 1-oxadiazolyl In one aspect, $R^1$ substituents include, but are not limited to, morpholinyl, pyrrolidinyl, piperidinyl, piperazinyl, pyrazolyl, imidazolyl, 1,3,4-oxadiazolyl, benzimidazolyl, benzothiazolyl, and benzoxazolyl each substituted with 0-3 $R^{1a}$.

In certain other aspects, compounds of Formula Ia wherein:

$R^4$ is a member selected from the group consisting of H, $C_3$-$C_7$ cycloalkyl, $C_1$-$C_6$ alkyl substituted with 0-1 $R^{20}$, wherein said $C_1$-$C_6$ alkyl may optionally contain a heteroatom selected from the group consisting of —O—, —S—, —S(=O)$_2$—;

each $R^{20}$ is independently a member selected from the group consisting of H, OH, C(=O)O$R^{15}$, C(=O)N$R^{16}R^{17}$, N$R^{12}R^{13}$, phenyl substituted with 0-3 $R^{14}$, 5- to 6-membered heteroaryl containing 1 to 4 heteroatoms each independently a member selected from the group consisting of N, O and S, wherein said heteroaryl is substituted with 0-3 $R^{14}$, $C_3$-$C_8$ heterocycle containing 1 to 2 heteroatoms each independently a member selected from the group consisting of N, O and S, wherein said heterocycle is substituted with 0-2 $R^{14}$ and is saturated or partially unsaturated, and $C_3$-$C_8$ cycloalkyl; and alternatively, $R^{19}$ and $R^8$ are taken together to form a 5- to 7-membered heterocyclic ring containing 1 nitrogen wherein said 5 to 7 membered heterocyclic ring is ortho-fused to Ar; wherein said 5- to 7-membered heterocyclic ring may be optionally substituted with 0-2 $R^{22}$ are also preferred.

In yet other aspects, compounds wherein:

$R^1$ is selected from group consisting of morpholinyl, pyrazolyl, imidazolyl, 1,3,4-oxadiazolyl, benzimidazolyl, benzothiazolyl, and benzoxazolyl substituted with 0-3 $R^{1a}$;

$R^2$ is selected from the group consisting of $C_1$-$C_6$ alkyl, and $C_1$-$C_2$ alkyl substituted with 1 $R^{2a}$;

$R^{2a}$ is selected from the group consisting of $C_3$-$C_7$ cycloalkyl substituted with 0-2 $R^{2b}$;

$R^4$ is a member selected from the group consisting of H, $C_3$-$C_5$ cycloalkyl, $C_1$-$C_6$ alkyl substituted with 0-1 $R^{20}$, wherein said $C_1$-$C_6$ alkyl may optionally contain a heteroatom selected from the group consisting of —O—, —S—, —S(=O)$_2$—; and each $R^{20}$ is independently a member selected from the group consisting of H, OH, C(=O)O$R^{15}$, C(=O)N$R^{16}R^{17}$, N$R^{12}R^{13}$, and phenyl substituted with 0-3 $R^{14}$ are also preferred.

In another preferred aspect, the present invention provides a compound according to Formula Ib:

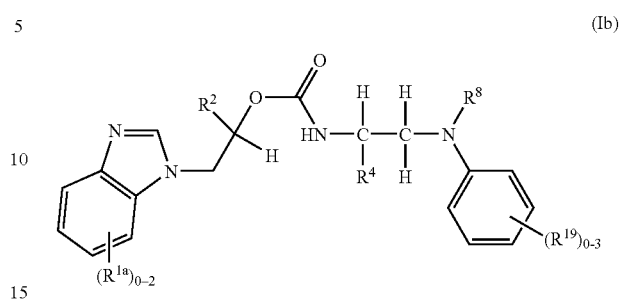

(Ib)

wherein:

each $R^{1a}$ is independently a member selected from the group consisting of F, Cl, Br, $C_1$-$C_6$ alkoxy, $C_1$-$C_3$ perfluoroalkyl, $C_1$-$C_3$ perfluoroalkoxy, a $C_1$-$C_6$ alkyl;

$R^4$ is a member selected from the group consisting of H, $CH_2CO_2R^{15}$, $C_1$-$C_6$ alkyl, cyclopropyl, benzyloxymethyl, benzyl, phenethyl, methanesulfonylmethyl, methylsulfonylethyl and ($C_1$-$C_4$ alkyl)-OH;

each $R^{15}$ is independently a member selected from the group consisting of H and $C_1$-$C_4$ alkyl.

In still another preferred aspect, the present invention provides a compound according to Formula Ic:

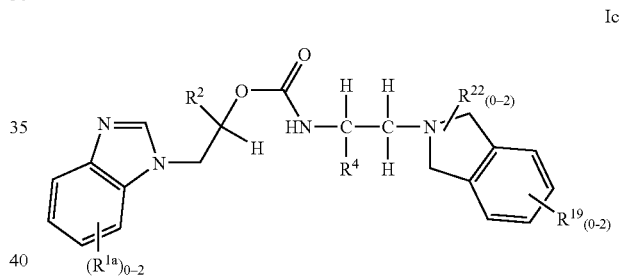

Ic

Preferred compounds of Formula I are set forth below:

1. 1-(R)-(5,6-dichloro-benzimidazol-1-ylmethyl)-3,3-dimethyl-butyl [2-(5-fluoro-2,3-dihydro-indol-1-yl)-1-(R)-hydroxymethyl-ethyl]carbamate;
2. 1-(S)-(5,6-dichloro-benzimidazol-1-ylmethyl)-3,3-dimethyl-butyl [2-(5-fluoro-2,3-dihydro-indol-1-yl)-1-(R)-hydroxymethyl-ethyl]carbamate;
3. 1-(5,6-dichloro-benzimidazol-1-ylmethyl)-2,2-dimethyl-propyl [2-(5-fluoro-2,3-dihydro-indol-1-yl)-1-(R)-hydroxymethyl-ethyl]carbamate;
4. 1-(S)-(benzimidazol-1-ylmethyl-3,3-dimethyl)-butyl [2-(5-fluoro-2,3-dihydro-indol-1-yl)-1-(S)-methyl-ethyl]carbamate;
5. 3,3-dimethyl-(S)-1-morpholin-4-ylmethyl-butyl [2-(5-fluoro-2,3-dihydro-indol-1-yl)-1-(S)-methyl-ethyl]carbamate;
6. 2-(benzimidazol-1-yl)-1-(S)-cyclopentylmethyl-ethyl [2-(5-fluoro-2,3-dihydro-indol-1-yl)-1-(S)-methyl-ethyl]carbamate;
7. 1-(S)-cyclopentylmethyl-2-(3-trifluoromethyl-pyrazol-1-yl)-ethyl [2-(4-difluoromethoxy-phenylamino)-1-(S)-methyl-ethyl]carbamate;
8. 1-(S)-cyclopentylmethyl-2-(5,6-dichloro-benzimidazol-1-yl)-ethyl [2-(4-difluoromethoxy-phenylamino)-1-(S)-methyl-ethyl]carbamate; and 9. 1-(S)-cyclopentylmethyl-2-(5,6-dichloro-benzimidazol-1-yl)-ethyl [2-(5-fluoro-2,3-dihydro-indol-1-yl)-1-(S)-methyl-ethyl]carbamate.
10. 1-(S)-cyclopentylmethyl-2-(5,6-dichloro-benzimidazol-1-yl)-ethyl [2-(4-trifluoromethoxy-phenylamino)-1-(S)-methyl-ethyl]carbamate.
11. 1-(S)-(benzimidazol-1-ylmethyl-3,3-dimethyl)-butyl [2-(5-fluoro-3,3-dimethyl-2,3-dihydro-indol-1-yl)-1-(S)-methyl-ethyl]carbamate.
12. 1-(S)-(benzimidazol-1-ylmethyl)-3,3-dimethyl-butyl [2-(5-fluoro-2,3-dihydro-indol-1-yl)-1-(R)-hydroxymethyl-ethyl]carbamate.

Compounds of the present invention are either obtained in the free form, or as a salt thereof if salt forming groups are present, or as esters if ester forming groups are present.

Compounds of the present invention that have acidic groups can be converted into salts with pharmaceutically acceptable bases, e.g., an aqueous alkali metal hydroxide, advantageously in the presence of an ethereal or alcoholic solvent, such as a lower alkanol. Resulting salts can be converted into the free compounds, e.g., by treatment with acids. These, or other salts can also be used for purification of the compounds obtained. Ammonium salts are obtained by reaction with the appropriate amine, e.g., diethylamine, and the like.

In certain aspects, compounds of the present invention having basic groups can be converted into acid addition salts, especially pharmaceutically acceptable salts. These are formed, for example, with inorganic acids, such as mineral acids, for example, sulfuric acid, a phosphoric or hydrohalic acid, or with organic carboxylic acids, such as ($C_1$-$C_4$) alkane carboxylic acids which, for example, are unsubstituted or substituted by halogen, for example, acetic acid, such as saturated or unsaturated dicarboxylic acids, for example, oxalic, succinic, maleic or famaric acid, such as hydroxycarboxylic acids, for example, glycolic, lactic, malic, tartaric or citric acid, such as amino acids, for example, aspartic or glutamic acid, or with organic sulfonic acids, such as ($C_1$-$C_4$)-alkylsulfonic acids (for example, methanesulfonic acid) or arylsulfonic acids which are unsubstituted or substituted (for example, by halogen). Preferred are salts formed with hydrochloric acid, methanesulfonic acid and maleic acid.

In view of the close relationship between the free compounds and the compounds in the form of their salts or esters, whenever a compound is referred to in this context, a corresponding salt or ester is also intended, provided such is possible or appropriate under the circumstances.

The compounds, including their salts, can also be obtained in the form of their hydrates, or include other solvents used for their crystallization.

The compounds of the present invention that comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding compounds of the present invention which comprise free hydroxyl groups. Suitable pharmaceutically acceptable prodrug esters are those derived from a carboxylic acid, a carbonic acid monoester or a carbamic acid, preferably esters derived from an optionally substituted lower alkanoic acid or an arylcarboxylic acid.

As will be apparent to one of skill in the art, certain compounds of the present invention possess asymmetric carbon atoms (optical centers) or double bonds; the racemates, diastereomers, enantiomers, geometric isomers and individual isomers are all intended to be encompassed within the scope of the present invention.

The present invention provides compounds which inhibit cathepsin S selectively. In certain preferred aspects, the present invention provides compounds which selectively inhibit cathepsin S in the presence of cathepsin isozymes, such as cathepsin A, B, C, D, E, F, G, H, K, L, M, O, P, Q, R, V, W and X. In a more preferred aspect, the present invention provides compounds which selectively inhibit cathepsin S in the presence of cathepsin K, L, B, or combinations thereof.

Compounds of the present invention useful for treating cathepsin S dependent conditions, preferably have cathepsin S inhibition constants less than 10 μM. More preferably, compounds of the present invention useful for treating cathepsin S dependent conditions have cathepsin S inhibition constants of less than 1.0 μM. Most preferably, compounds of the present invention useful for treating cathepsin S dependent conditions have cathepsin S inhibition constants of less than 0.1 μM.

In a preferred aspect, compounds of the present invention that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

IV. Compositions

The pharmaceutical compositions according to the invention are those suitable for enteral, such as oral or rectal, transdermal, topical, and parenteral administration to mammals, including humans, to inhibit cathepsin S activity, and for the treatment of cathepsin S dependent disorders, in particular chronic neuropathic pain (see, WO 03/020287), Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

More particularly, the pharmaceutical compositions comprise an effective cathepsin S inhibiting amount of a compound of the present invention.

The pharmacologically active compounds of the present invention are useful in the manufacture of pharmaceutical compositions comprising an effective amount thereof in conjunction or mixture with excipients or carriers suitable for either enteral or parenteral application.

Preferred are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical formulations contain an effective cathepsin S inhibiting amount of a compound of the present invention as defined above, either alone or in combination with another therapeutic agent.

In conjunction with another active ingredient, a compound of the present invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg of the active ingredient.

In one aspect, the pharmaceutical composition of the present invention provides a compound according to Formula I as defined above or a pharmaceutically acceptable salt or prodrug thereof, and a pharmaceutically acceptable excipient.

In a preferred aspect, the pharmaceutical composition of the present invention provides a compound according to Formula Ia as defined above.

In a preferred aspect, the pharmaceutical composition of the present invention provides a compound according to Formula Ib as defined above.

In certain aspects, the present invention provides compositions that comprise compounds of the present invention and pharmaceutically acceptable excipients, which selectively inhibit cathepsin S in the presence of other cathepsin isozymes. In a more preferred aspect, the present invention provides compositions which selectively inhibit cathepsin S in the presence of cathepsin K, L, B, or combinations thereof.

In another aspect of the present invention, compositions of the present invention useful for treating cathepsin S dependent conditions, preferably have cathepsin S inhibition constants less than 10 µM. More preferably, compositions of the present invention useful for treating cathepsin S dependent conditions have cathepsin S inhibition constants of less than 1.0 µM. Most preferably, compositions of the present invention useful for treating cathepsin S dependent conditions have cathepsin S inhibition constants of less than 0.1 µM.

In a preferred aspect, compositions of the present invention utilize compounds that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

V. Methods

In view of their activity as inhibitors of cathepsin S, compounds of the present invention are particularly useful in mammals as agents for treatment and prophylaxis of diseases and medical conditions involving elevated levels of cathepsin S. For example, the compounds of the present invention are useful in treating Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

Beneficial effects are evaluated in in vitro and in vivo pharmacological tests generally known in the art, and as illustrated herein.

The above cited properties are demonstrable in in vitro and in vivo tests, using advantageously mammals, e.g., rats, mice, dogs, rabbits, monkeys or isolated organs and tissues, as well as mammalian enzyme preparations, either natural or prepared by, e.g., recombinant technology. Compounds of the present invention can be applied in vitro in the form of solutions, e.g., preferably aqueous solutions or suspensions, and in vivo either enterally or parenterally, preferably orally, e.g., as a suspension or in aqueous solution, or as a solid capsule formulation. The dosage in vitro may range between about $10^{-5}$ molar and $10^{-9}$ molar concentrations. The dosage in vivo may range, depending on the route of administration, between about 0.1 and 100 mg/kg.

The antiarthritic efficacy of the compounds of the present invention for the treatment of rheumatoid arthritis can be determined using models such as, or similar to, the rat model of adjuvant arthritis, as described previously (R. E. Esser, et. al. *J Rheumatology* 1993, 20, 1176). The efficacy of the compounds of the present invention for the treatment of osteoarthritis can be determined using models such as, or similar to, the rabbit partial lateral meniscectomy model, as described previously (Colombo et al. *Arth. Rheum.* 1993, 26, 875-886). The efficacy of the compounds in the model can be quantified using histological scoring methods, as described previously (O'Byrne et al. *Inflamm. Res.* 1995, 44, S 177-S118).

The present invention also relates to methods of using compounds of the present invention and their pharmaceutically acceptable salts, or pharmaceutical compositions thereof, in mammals for inhibiting cathepsin S, and for the treatment of cathepsin S dependent conditions, such as the cathepsin S dependent conditions described herein, e.g., inflammation, rheumatoid arthritis and osteoarthritis.

In a preferred aspect, the present invention relates to a method of treating rheumatoid arthritis, osteoarthritis, and inflammation (and other diseases as identified above) in mammals comprising administering to a mammal in need thereof, a correspondingly effective amount of a compound of the present invention.

In a preferred aspect, the method of the present invention provides a compound according to Formula I as defined above.

In a preferred aspect, the method of the present invention provides a compound according to Formula Ia as defined above.

In another preferred aspect, the method of the present invention provides a compound according to Formula Ib as defined above.

Methods of the present invention useful for treating cathepsin S dependent conditions, preferably use compounds that have cathepsin S inhibition constants less than 10 µM. More preferably, methods of the present invention useful for treating cathepsin S dependent conditions use compounds that have cathepsin S inhibition constants of less than 1.0 µM. Most preferably, methods of the present invention useful for treating cathepsin S dependent conditions use compounds that have cathepsin S inhibition constants of less than 0.1 µM.

Moreover, the present invention relates to a method of selectively inhibiting cathepsin S activity in a mammal which comprises administering to a mammal in need thereof, an effective cathepsin S inhibiting amount of a compound of the present invention. In a preferred aspect, the methods of the present invention use compounds that selectively inhibit cathepsin S in the presence of a cathepsin isozyme, such as cathepsin A, B, C, D, E, F, G, H, K, L, M, O, P, Q, R, V, W and X. In a more preferred aspect, methods of the present invention use compounds that selectively inhibit cathepsin S in the presence of cathepsin K, L, B, or combinations thereof.

In a preferred aspect, methods of the present invention use compounds that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

VI. EXAMPLES

A. General Procedure

Unless otherwise stated glassware was air dried prior to use with no special precautions taken for drying. All solvents stated as anhydrous were purchased that way from the manufacturer and used as received. All other purchased reagents were used as received. Unless otherwise stated, all reactions were carried out under a positive pressure of nitrogen. Silica gel chromatography was performed using pre-packed cartridges and an instrument for making a linear solvent gradient along with automated fraction collection. $^1$H NMR spectral data were reported as follows: chemical shift on the δ scale (using residual protio solvent as the internal standard), multiplicity (s=singlet, d=doublet, t=triplet, q=quartet, m=multiplet), integration and coupling constant in hertz. $^{13}$C spectra were recorded as APT experiments and were reported in ppm with residual solvent for internal standard. $^1$H and $^{13}$C NMR spectral data were recorded on a Brucker 400 MHz NMR spectrometer. Microwave assisted reactions were performed on Emrys Optimizer from Personal Chemistry, Sweden.

Reference 1. Synthesis of (S)-2-(4-Methoxy-phenylamino)-1-methyl Ethyl Amine.

Step A: Preparation of (S)-2-(tert-Butoxycarbonylamino)-propionaldehyde. (S)-(−)-2-(tert-Butoxycarbonylamino)-1-propanol (523 mg, 2.98 mmol, 1.0 equiv.) was dissolved in 45 mL methylene chloride in a 100 mL r.b. flask with a magnetic stir bar. To this clear homogeneous solution, Dess-Martin periodinane (1.523 g, 3.591 mmol, 1.2 equiv.) was added in one part and the cloudy white reaction mixture was allowed to stir at room temperature for 2 h. Thin-layer chromatography monitored the reaction to completion. The reaction mixture was diluted with 100 mL ethyl acetate. Sodium bisulfite solution (2 M, 20 mL) was added to the reaction mixture and the organic layer was separated. The aqueous layer was washed with 3×30 mL EtOAc. The combined organic layers were washed with 50 mL 1 M NaOH, followed by saturated NaCl (30 mL) and dried over MgSO$_4$. Filtration and rotary evaporation produced the desired product as a yellow oil (475 mg, 92% yield, R$_f$=0.63, 1:1 hexanes/ethyl acetate).

Step B: Preparation of [2-(4-methoxy-phenylamino)-(1S)-methyl-ethyl]-carbamic acid tert-butyl ester. (S)-2-(tert-Butoxycarbonylamino)-propionaldehyde (473 mg, 2.74 mmol) and p-anisidine (1.031 g, 8.371 mmol, 3.0 equiv.) was dissolved in 45 mL of MeOH at 0° C. in a 100 mL r.b. flask with a magnetic stir bar. Optionally, acetic acid (469 µL, 8.21 mmol, 3.0 equiv.) can be added via syringe to assist in the reaction. To the stirring dark colored solution was added sodium cyanoborohydride (326 mg, 5.82 mmol, 1.89 equiv.). Gas evolution and disappearance of color were observed. The reaction was allowed to slowly warm to room temperature with stirring over 30 minutes and the reaction was monitored by LC/MS. At the completion of the reaction, the mixture was quenched with 1 M NaOH, and extracted 3×50 mL ethyl acetate. The resulting organics were washed with 50 mL saturated NaHCO$_3$, 40 mL saturated NaCl, and dried over MgSO$_4$. Evaporation of ethyl acetate provided 728 mg of a brown oil. Purification by automated ISCO chromatography provided a clear oil of [2-(4-methoxy-phenylamino)-(1S)-methyl-ethyl]-carbamic acid tert-butyl ester (583 mg, 2.079 mmol, 76% yield). HPLC-MS calcd. for $C_{15}H_{24}N_2O_3$ (M+H$^+$) 281.2, found 281.5. $^1$H NMR (CDCl$_3$, 400 MHz) δ 1.21 (d, 6H, J=6.6 Hz), 1.47 (s, 9H), 3.05 (dd, 1H, J=12.2, 7.3 Hz), 3.13 (dd, 1H, J=12.2, 4.6 Hz), 3.76 (s, 3H), 3.93 (broad s, 1H), 4.62 (broad s, 1H), 6.60 (d, 2H, J=6.8 Hz), 6.80 (2H, d, J=6.8 Hz).

Step C: [2-(4-Methoxy-phenylamino)-(1S)-methyl-ethyl]-carbamic acid tert-butyl ester (383 mg, 1.37 mmol) was added to 10 mL of a trifluroacetic acid solution (10 v/v % in methylene chloride) at room temperature in a 25 mL r.b. flask with a magnetic stirbar. The reaction turns dark purple/black in color after 5 minutes. The reaction is allowed to stir at room temperature until the reaction is judged complete by HPLC/MS. The solvent is removed by evaporation and to provide 2-(4-Methoxy-phenylamino)-(1S)-methyl-ethyl-ammonium; trifluoro-acetate salt as a brown oil (394 mg, 1.34 mmol, 98% yield) and used directly in the next reaction. HPLC-MS calcd. for $C_{10}H_{16}N_2O$ (M+H$^+$) 181.1, found 181.5.

Reference 2. (R)-3-Benzyloxy-N$^1$-(4-methoxy-phenyl)-propane-1,2-diamine.

Step A: N-Boc-OBn-Serine (750 mg, 2.54 mmol), p-anisidine (344 mg, 2.79 mmol) and HOBt (377 mg, 2.79 mmol) were charged to a 50 mL roundbottom flask and treated with $CH_2Cl_2$ (6 mL). The reaction was then treated with EDCI (535 mg, 2.79 mmol) and allowed to stir for 2 hours. The reaction was then diluted with ethyl acetate and extracted twice with water, twice with 1 M HCl and twice with 1 M NaOH. The organics were then dried over $MgSO_4$ and the solvent was removed to afford 450 mg (44%) of a white solid: $^1$H NMR (CDCl$_3$, 400 MHz) a 1.49 (s, 9H), 3.63-3.72 (m, 1H), 3.81 (s, 3H), 4.00-4.08 (m, 1H), 4.47-4.50 (m, 1H), 4.55-4.70 (m, 2H), 5.45-5.60 (m, 1H), 6.87 (d, 2H, J=8.8), 7.30-7.41 (m, 7H), 8.20-8.33 (m, 1H); HPLC-MS calcd. for $C_{22}H_{28}N_2O_5$ (M+H$^+$) 401.2, found 401.4.

Step B: The product from Step A (400 mg, 1.00 mmol) was added to an ice cold solution of borane (1 M) in THF. The cooling bath was removed and the reaction was allowed to stir for 24 h at which point the excess reagent was quenched using 5% NaHSO$_4$. The reaction was diluted with ethyl acetate and extracted twice with 1 M NaOH. The organics were dried over MgSO$_4$ and the solvent was removed. The resulting residue contained material that was missing the Boc group and some material that still had it (by HPLC-MS). The oil was treated with MeOH (2 mL) and 4 M HCl (2 mL) and stirred for 3 hours. The solvent was then removed and the reaction was partitioned between ethyl acetate and 1 M NaOH. The aqueous phase was extracted twice more with ethyl acetate and the combined organics were dried over MgSO$_4$ and the solvent was removed.

Reference 3. Synthesis of (S)-N-1-(4-trifluoromethoxy-phenyl)-propane-1,2-diamine.

Step A: (S)-2-(benzylcarbonylamino)-propionaldehyde.

(S)-2-(benzylcarbonylamino)-propanol (5.00 g, 23.9 mmol) was dissolved in CH$_2$Cl$_2$ (200 mL) and treated with Dess-Martin periodinane (12.26 g, 1.1 eq). The mixture was stirred for 2 hours, then quenched with sodium thiosulphate, and the solvent removed in vacuo. The residue was then separated between sodium hydroxide (1M, 500 mL) and ethyl acetate (500 mL). The organics were washed with brine, dried (MgSO$_4$) and evaporated in vacuo to yield a clear oil which was used immediately in the next step without further purification.

Step B:[1-(S)-Methyl-2-(4-trifluoromethoxy-phenylamino)-ethyl]-carbamic acid benzyl ester.

(S)-2-(benzylcarbonylamino)-propionaldehyde was dissolved in methanol (300 mL). Acetic acid (4 mL, 2.9 eq) was added and the mixture treated with 4-trifluoromethoxy aniline (9.6 mL, 3 eq) and stirred for 15 minutes then sodium cyanoborohydride (4.36 g, 2.9 eq) was added with some effervescence. The mixture was stirred for 3 hours, and then the solvent reduced in vacuo. This was then separated between hydrochloric acid (1M, 500 mL×2) and ethyl acetate (500 mL). The organics were washed with sodium bicarbonate (500 mL), brine (500 mL), dried (MgSO$_4$) and evaporated in vacuo to give a clear oil which was purified by silica gel chromatography eluted with a gradient of 0-100% ethyl acetate/hexane.

Step C: (S)—N1-(4-Trifluoromethoxy-phenyl)-propane-1,2-diamine.

[1-(S)-Methyl-2-(4-trifluoromethoxy-phenylamino)-ethyl]-carbamic acid benzyl ester (23.9 mmol) was dissolved in ethanol (200 mL) then placed under nitrogen. 10% Palladium on carbon was added (0.5 g) and the mixture was stirred under hydrogen (atmospheric pressure) overnight. When reaction was complete, the mixture was filtered through celite. The celite was washed with ethanol (5×50 mL) then evaporated in vacuo to give a brown oil (4.03 g, 17.21 mmol, 72% yield over 3 steps).

Reference 4. Synthesis of 2,2-dimethyl-5-fluoroindoline.

Step A: A solution of N-Boc-4-fluoroaniline (9.02 g, 42.7 mmol) in THF (112 mL) was cooled to −60° C. using a cryocool instrument. The solution was treated with 1.7 M t-BuLi in pentane (63 mL, 106.7 mmol) dropwise. After the first equivalent of base was consumed, a yellow solution formed. The reaction was allowed to warm to −20° C. and was stirred at that temperature for 2.5 hours. The reaction was then treated with a solution of methallyl bromide (5.67 g, 42.7 mmol) in THF (35 mL) dropwise and stirred for an additional 1.5 hours at −20° C. The reaction was then quenched by addition of water. After coming to room temperature, the reaction was treated with ethyl acetate and extracted with water and brine, dried over MgSO$_4$ and filtered. The solvent was then removed and the residue was purified on silica gel using a gradient of 0-25% ethyl acetate in hexane to afford 11.3 g (80% yield) of [4-Fluoro-2-(2-methyl-allyl)-phenyl]-carbamic acid tert-butyl ester as a white solid; $^1$H NMR (CDCl$_3$, 400 MHz) δ 1.50 (s, 9H), 1.72 (s, 3H), 3.28 (s, 2H), 4.71 (s, 1H), 4.92 (s, 1H), 6.32-6.50 (m, 1H), 6.86 (dd, 1H, J=3.0, J$_2$=9.1), 6.93 (ddd, 1H, J=3.0, J$_2$=8.5, J$_3$=11.5), $_{7.65}$-$_{7.82}$ (m, 1H); HPLC-MS calcd. for $C_{15}H_{20}FNO_2$ (M+H$^+$-tBu) 210.1, found 210.3.

Step B: A sample of [4-Fluoro-2-(2-methyl-allyl)-phenyl]-carbamic acid tert-butyl ester (1.10 g, 4.14 mmol) was treated with anisole (5 mL), dichloromethane (5 mL) and trifluoroacetic acid (5 mL) and stirred for 4 hours. The solvent was removed and the reaction was transferred to a microwave reaction vial using methanesulfonic acid (3 mL). The reaction was heated to 170° C. for 10 minutes. The reaction was cooled to room temperature and quenched into excess stirring 1 M NaOH. The aqueous phase was extracted twice with ethyl acetate and the combined organics were dried over MgSO$_4$ and filtered. The resulting oil was purified on silica gel using a gradient of 0-70% t-butyl ethyl ether and hexane to afford 450 mg (66% yield) of 2,2-dimethyl-5-fluoroindoline; $^1$H NMR (CDCl$_3$, 400 MHz) δ 1.08 (s, 6H), 2.58 (s, 2H), 6.24 (dd, 1H, J=4.4, J$_2$=8.4), 6.43-6.48 (m, 1H), 6.53-6.56 (m, 1H); HPLC-MS calcd. for $C_{10}H_{12}FN$ (M+H$^+$) 166.1, found 166.4.

Reference 5. Synthesis of 3,3-dimethyl-5-fluoroindoline.

According to the procedure described in S. Coulton et al. WO9925709 with the following modifications. N-(4-Fluorophenyl)-N-(2-methyl-allyl)-acetamide (5 grams, 24.12 mmol) was added to a microwave tube with aluminum trichloride (7 grams, 52.4 mmol). The tube was capped and heated to 150° C. for 20 minutes under microwave. The slurry was worked up with water and ethyl acetate, the organic layer was extracted with 3 washes of saturated sodium bicarbonate solution and the organic layer was dried over magnesium sulfate. The solution was then filtered and rotary evaporated to yield pure 1-(5-Fluoro-3,3-dimethyl-2,3-dihydro-indol-1-yl)-ethanone in quantitative yield. This was converted to the free indoline by suspending the entire 5 grams of product in 20 mL of 6 M HCl and heating in a microwave to 200° C. for 10 minutes. The resulting 5-Fluoro-3,3-dimethyl-2,3-dihydro-1H-indole crystallized on cooling as the hydrochloride salt in quantitative yield. This material was identical to the previously reported compound.

Reference 6. Synthesis of (S)-[1-Cyclopropyl-2-(5-fluoro-3,3-dimethyl-2,3-dihydro-indol-1. -yl)-ethyl]-carbamic Acid Benzyl Ester Step A: (S)-cyclopropyl glycine was prepared according to a modified procedure from that reported in D. J. Bayston et al. U.S. Pat. No. 6,191,306. A sample of (R)-phenethyl-(S)-cyclopropyl glycine (16.8 g, 76.7 mmol) was treated with THF (200 mL), water (100 mL) and 10% Pd/C (4.76 g). To the stirring mixture was added formic acid (17 mL) and the reaction was stirred overnight. The catalyst was then removed by filtration through a pad of celite and the solvent was removed by rotary evaporation. The material was co-evaporated with methanol several times and dried under vacuum to afford 4.75 g (54% yield) of the desired material as a solid which was used without further purification.

The material from the previous step (4.75 g, 41 mmol) was dissolved in 130 mL of 1 N NaOH and treated with benzyl chloroformate (5.92 g, 49.5 mmol) with vigorous stirring. The reaction was stirred overnight and then extracted with dichloromethane twice. The organics were discarded and the aqueous phase was acidified with conc. HCl and extracted with dichloromethane three times. The combined organics were dried over $MgSO_4$ and the solvent was removed to afford 7.38 g (72% yield) of the (S)-benzyloxycarbonylamino-cyclopropyl-acetic acid as a white solid.

Step B: A solution of(S)-benzyloxycarbonylamino-cyclopropyl-acetic acid (3.2 g, 12.8 mmol) in THF (20 mL) was cooled in an ice/water bath and treated with a 1 M solution of $BH_3$ in THF (16.7 mL, 16.7 mmol). The reaction was stirred for 4 hours and then treated with 1 M HCl until the bubbling ceased. The reaction was stirred overnight and the organic solvent was removed by rotary evaporation. The residue was treated with ethyl acetate and transferred to a separatory funnel. The aqueous phase was discarded and the organics were washed twice with 1 M NaOH, dried over $MgSO_4$ and the solvent was removed. The residue was purified on silica gel using a gradient of 0-100% ethyl acetate in hexane to afford 1.5 g (50% yield) of (S)-(1-Cyclopropyl-2-hydroxy-ethyl)-carbamic acid benzyl ester as a white solid; $^1$H NMR ($CDCl_3$, 400 MHz) δ 0.26-0.37 (m, 1H), 0.34-0.44 (m, 1H), 0.47-0.61 (m, 2H), 0.83-0.94 (m, 1H), 2.95-3.04 (m, 1H), 3.70 (dd, 1H, J=5.8, $J_2$=11.1), 3.79-3.88 (m, 1H), 5.00-5.12 (m, 1H), 5.10 (s, 2H), 7.29-7.31 (m, 5H); HPLC-MS calcd. for $C_{13}H_{17}NO_3$ (M+H$^+$) 236.1, found 236.3.

Step C: (S)-[1-Cyclopropyl-2-(5-fluoro-3,3-dimethyl-2,3-dihydro-indol-1-yl)-ethyl]-carbamic acid benzyl ester was prepared in 67% yield an analogous manner to reference 3 except that the alcohol from the previous step and 1 equivalent of 3,3-dimethyl-5-fluoroindoline (WO 9925709) were used as coupling partners; HPLC-MS calcd. for C23H27FN2O2 (M+H+) 383.2, found 383.4.

Reference 7. Synthesis of 5-fluoro-3,3-spirocyclopropyl-indoline

Step A: A solution of 5-fluoroisatin (5 g, 30.2 mmol) in DMF (60 mL) was cooled in an ice/water bath and treated with sodium hydride (1.44 g, 60.6 mmol) portionwise. The reaction was stirred for 15 minutes after the addition of the last portion and then treated with p-methoxybenzyl chloride (5.32 g, 45.3 mmol) and allowed to stir for 1 hour. The reaction was then quenched by slow addition of excess methanol. After bubbling had stopped, the reaction was poured into water (100 mL) and extracted twice with ethyl acetate. The organics were combined, dried over $MgSO_4$ and the solvent was removed. The residue was purified by silica gel chromatography using a gradient of 0-100% ethyl acetate in hexane to afford 7.1 g (82%) of 5-Fluoro-1-(4-methoxy-benzyl)-1H-indole-2,3-dione; $^1$H NMR ($CDCl_3$, 400 MHz) δ 3.79 (s, 3H), 4.86 (s, 2H), 6.75 (dd, 1H, J=3.6, $J_2$=8.6), 6.84-6.90 (m, 2H), 7.19 (ddd, 1H, J=$J_2$=8.6, $J_3$=3.6), 7.22-7.27 (m, 1H), 7.26-7.31 (m, 2H); HPLC-MS calcd. for $C_{16}H_{12}FNO_3$ (M+H$^+$) 286.1, found 286.3.

Step B: A solution of 5-fluoro-1-(4-methoxy-benzyl)-1H-indole-2,3-dione (7.1 g, 24.9 mmol) in hydrazine hydrate (35 mL) and ethanol (15 mL) was refluxed overnight, diluted with water and extracted twice with ethyl acetate. The combined organics were dried over $Na_2SO_4$, filtered and concentrated. The residue was purified by silica gel chromatography using a gradient of 0-100% ethyl acetate in hexane to afford 6.1 g (90%) of 5-fluoro-1-(4-methoxy-benzyl)-1,3-dihydro-indol-2-one; $^1$H NMR ($CDCl_3$, 400 MHz) δ 3.59 (s, 2H), 3.77 (s, 3H), 4.83 (s, 2H), 6.63 (dd, 1H, J=4.2, $J_2$=8.6), 6.82-6.91 (m, 3H), 6.96-7.01 (m, 1H), 7.19-7.23 (m, 1H), 7.27-7.31 (m, 1H); HPLC-MS calcd. for $C_{16}H_{14}FNO_2$ (M+H$^+$) 272.1, found 272.3.

Step C: A solution of 5-fluoro-1-(4-methoxy-benzyl)-1,3-dihydro-indol-2-one (6.12 g, 22.6 mmol) in DMF (65 mL) was cooled in an ice/water bath and treated with dibromo-ethane (6.35 g, 33.8 mmol) followed by sodium hydride (1.09 g, 45 mmol) portionwise. After stirring at 0° C. for 1 hour, the reaction was cooled to −78° C. and treated with excess methanol. After bubbling had stopped, the reaction was poured into water (100 mL) and extracted twice with ethyl acetate. The organics were combined, dried over $Na_2SO_4$ and the solvent was removed. The residue was purified by silica gel chromatography using a gradient of 0-100% ethyl acetate in hexane to afford 4.1 g (61%) of 5-fluoro-1-(4-methoxy-benzyl)-siprocyclopropyloxindole; $^1$H NMR ($CDCl_3$, 400 MHz) δ 1.54 (dd, 2H, J=4.0, $J_2$=7.8), 1.83 (dd, 2H, J=4.3, $J_2$=8.1), 3.77 (s, 3H), 4.91 (s, 2H), 6.57 (dd, 1H, $J_1$=2.5, $J_2$=8.0), 6.69 (dd, 1H, J=4.2, $J_2$=8.5), 6.81 (dd, 1H, J=2.5, $J_2$=9.3), 6.83-6.87 (m, 2H), 7.22-7.25 (m, 2H); HPLC-MS calcd. for $C_{18}H_{16}FNO_2$ (M+H$^+$) 298.1, found 298.3.

Step D: A solution of 5-fluoro-1-(4-methoxy-benzyl)-siprocyclopropyloxindole (3.38 g, 11.4 mmol) in TFA (20 mL) was stirred at 60° C. overnight. The solvent was then removed and the reaction was diluted with ethyl acetate and washed with saturated aqueous $NaHCO_3$ until the washings were neutral. The organic phase was then washed with brine, dried over $Na_2SO_4$ and the solvent was removed. The residue was purified by silica gel chromatography using a gradient of 0-100% ethyl acetate in hexane to afford 1.94 g (96%) of 5-fluoro-siprocyclopropyloxindole; $^1$H NMR (MeOD, 400 MHz) δ 1.76-1.86 (m, 4H), 6.91-6.94 (m, 1H), 7.07-7.11 (m, 2H); HPLC-MS calcd. for $C_{10}H_8FNO$ (M+H$^+$) 178.2, found 178.3.

Step E: A sample of 5-fluoro-siprocyclopropyloxindole (172 mg, 97 μmol) was cooled in an ice/water bath and treated with a 1.0 M solution of LAH (1.94 ml, 1.9 mmol). The reaction was stirred at room temperature for 15 minutes and then at 50° C. for 3 hours and finally was cooled back down with an ice/water bath. The reaction was treated with 1 M NaOH (1.9 mL) followed by water (1.9 mL). The reaction was filtered over celite and dried over $MgSO_4$. After filtration, the solvent was removed and the crude material of 5-fluoro-siprocyclopropylindoline was used without purification.

In addition, synthesis of other 3,3-spiro-cycloalkylindolines are also described in (1) Jackson, A. H. et al. Tetrahedron (1968), 24(1), 403-13; (2) Jansen, A. B. A. et al. Tetrahedron (1965), 21(6), 1327-31; (3) Bermudez, J. et al. J. Med. Chem. (1990), 33(7), 1929-32; (4) Nishio, T. et al. Helv. Chim. Acta (1990), 73(6), 1719-23; (5) Nishio, T. et al. J. Chem. Soc., Perkin Trans 1 (1991), (1), 141-3; (6) Kucerovy, A. et al. Synth. Commun. (1992), 22(5), 729-33; (7) Kato, M. et al. Chem. Pharm. Bull.(1995), 43(8), 1351-7.

Reference 8. Synthesis of 2,2,5-trifluoroindoline.

Step A: 5-Fluoro-1H-indole-2,3-dione (956 mg, 5.79 mmol, 1 eq) was added as a solution in dry DMF to a stirred slurry of sodium hydride (278 mg, 11.6 mmol, 2 eq) in dry DMF drop wise over 15 minutes under an inert atmosphere with adequate pressure release to accommodate $H_2$ evolution. The resulting mixture was stirred for 1 hour and p-methoxybenzyl chloride was added via syringe to the reaction. The solution was then stirred ca 2 hours and worked up by addition of water followed by extraction into ethyl acetate. The organic layer was washed twice with water and then dried over $MgSO_4$. Column chromatography with ethyl acetate/hexane afforded 5-Fluoro-1-(4-methoxybenzyl)-1H-indole-2,3-dione as a red solid (1.3 g, 80% yield). $^1$H NMR (CDCl$_3$) δ (ppm): 7.3-7.24 (m, 3H), 7.20 (td, J=8.7, 2.7 Hz, 1H), 6.9-6.86 (m, 2H), 6.76 (dd, J=8.6, 3.6 Hz, 1H), 3.81 (s, 2H), 3.78 (s, 3H). LC/MS=286.1 (M+1).

Step B: The product from step A (200 mg, 0.701 mmol, 1 eq) was dissolved in 10 mL of dry DCM and placed under and inert atmosphere. DAST (339 mg, 2.103 mmol, 3 eq) was added via syringe and the reaction was stirred overnight. The reaction was worked up by addition of saturated aqueous sodium bicarbonate and the organic layer was dried over $MgSO_4$, filtered, and rotary evaporated to dryness. The resulting crude material was purified by flash chromatography using ethyl acetate/hexane as a solvent system. $^1$H NMR (CDCl$_3$) δ (ppm): 7.3-7.28 (m, 1H), 7.22 (d, J=8.7 Hz, 2H), 7.09 (td, J=8.7, 1.3 Hz, 1H), 6.87 (d, J=8.7 Hz, 2H), 6.73 (m, 1H), 4.83 (s, 2H), 3.79 (s, 3H). LC/MS=308.1 (M+1).

Step C: The product from step B (1.178 g, 3.83 mmol, 1 eq) was dissolved in 75 mL of dry THF and placed under an inert atmosphere. LiAlH$_4$ (291 mg, 7.66 mmol, 2 eq) was added as a solid under a positive pressure of $N_2$ at −78° C. The reaction was allowed to stir at this temperature for 30 min and then allowed to warm to room temp over a period of 6 hours. The reaction was worked up by addition of water dropwise followed by 4 equivalents of aqueous KOH. The slurry was diluted with 500 mL of water and extracted with 2×200 mL portions of ethyl acetate. The organic layers were combined, dried over $MgSO_4$, filtered, and rotary evaporated to dryness. The resulting crude material was purified by flash chromatography using ethyl acetate/hexane as a solvent system yielding 320 mg of pure material (28%). $^1$H NMR (CD$_3$OD) δ (ppm): 7.21 (d, J=8.8 Hz, 2H), 7.06 (dd, J=8.2, 1.3 Hz, 1H), 6.89 (m, 1H), 6.84 (d, J=8.7 Hz, 2H), 6.77 (dd, J=8.6, 4.3 Hz, 1H), 4.83 (s, 2H), 3.73 (s, 3H), 3.12 (s, 2H). LC/MS=294.1 (M+1).

Step D: The product from step C (50 mg, 0.1704 mmol, 1 eq) was taken up in 1 mL of TFA. The solution was placed in a microwave tube, sealed, and heated to 175° C. for 5 minutes. The resulting black solution was neutralized with saturated sodium bicarbonate and extracted with 2×50 mL portions of ethyl acetate. The organic layers were dried over $MgSO_4$, filtered, and rotary evaporated to dryness. The resulting solid was dissolved in a 50:50 mix of DMSO/MeOH and purified by prep HPLC. Yield 23.8 mg of white solid (81%). $^1$H NMR (DMSO D$_6$) δ (ppm): 10.41 (s, 1H), 7.13 (dd, J=8.6, 2.4 Hz, 1H), 7.01 (td, J=8.6, 2.7 Hz, 1H), 6.8 (dd, J=8.5, 4.5 Hz, 1H), 3.5 (s, 2H).

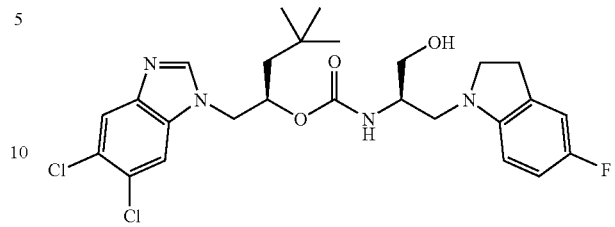

Example 1

1-(R)-(5,6-Dichloro-benzimidazol-1-ylmethyl)-3,3-dimethyl-butyl [2-(5-fluoro-2,3-dihydro-indol-1-yl)-1-(R)-hydroxymethyl-ethyl]carbamate;

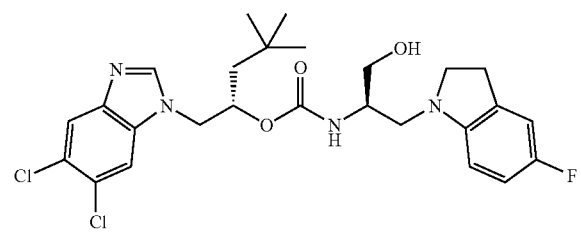

Example 2

1-(S)-(5,6-Dichloro-benzimidazol-1-ylmethyl)-3,3-dimethyl-butyl [2-(5-fluoro-2,3-dihydro-indol-1-yl)-1-(R)-hydroxymethyl-ethyl]carbamate

Step A: Preparation of 1,2 epxoy-4,4-dimethylpentane. A solution of 4,4-dimethyl-1-pentene (8.05 g, 82 mmol) in CH$_2$Cl$_2$ (45 mL) was treated with methyltrioxorhenium (0.10 g, 0.41 mmol) and put into a water bath and stirring was initiated. The reaction mixture was treated with 3-cyanopyridine (853 mg) and stirred until the material dissolved. A solution of 31% aqueous hydrogen peroxide (11.7 mL, 107 mmol) was then added dropwise over the course of about 30 minutes, keeping the temperature at 20 to 25° C. The reaction was allowed to stir overnight. The contents of the flask were then transferred to a seperatory funnel. A separate flask was charged with 15 mg of MnO$_2$ and a stir bar and cooled with an ice bath. The organic layer was slowly poured into this flask, allowing ample time for the hydrogen peroxide to be quenched. After 15 minutes of stirring, sodium sulfate (20 g) was added and stirring was continued for an additional 15 minutes. The solution was then transferred to a 100 mL pear shaped flask. The CH$_2$Cl$_2$ was distilled off at atmospheric pressure through a Vigreaux column. After the initial distillation, the Vigreaux was removed and replaced with a regular short path distillation head. The flask was heated to 120° C. and a mild vacuum was applied to transfer over 7.7 g (82%) of product as a colorless liquid: $^1$H NMR (CDCl$_3$, 400 MHz) δ 0.94 (s, 9H), 1.31 (dd, 1H, J=5.4, J$_2$=14.0), 1.38 (dd, 1H, J=6.4, J$_2$=14.0), 2.35 (dd, 1H, J=2.8, J$_2$=5.1), 2.67-2.71 (m, 1H), 2.86-2.93 (m, 1H).

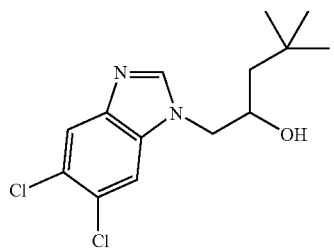

Step B: Synthesis of 1-(5,6-Dichloro-benzimidazol-1-yl)-4,4-dimethyl-pentan-2-ol: A large (2-5 mL) microwave reactor flask was charged with 5,6-dichlorobenzimidazole (700 mg, 3.74 mmol), the oxirane obtained from Step A (600 mg, 3.37 mmol), powdered anhydrous K$_2$CO$_3$ (517 mg, 3.74 mmol) and DMF (2 mL). The reaction mixture was then heated to 160° C. for 5 minutes. The reaction mixture was then diluted with ethyl acetate and extracted with water once and 1 M NaOH twice. The organics were dried over MgSO$_4$ and the solvent was removed. The residue was purified on silica gel using ethyl acetate as eluent to afford 475 mg (42%) of product as a colorless solid: $^1$H NMR (CDCl$_3$, 400 MHz) δ 0.99 (s, 9H), 1.39 (dd, 1H, J=2.4, J$_2$=14.4), 1.48 (dd, 1H, J$_1$=8.4, J$_2$=14.4), 3.63-3.71 (m, 1H), 3.90 (dd, 1H, J=8.9, J$_2$=14.4), 4.00 (dd, 1H, J=2.8, J$_2$=14.4), 4.03-4.12 (m, 1H), 7.40 (s, 1H), 7.42 (s, 1H), 7.74 (s, 1H); HPLC-MS calcd. for C$_{14}$H$_{18}$Cl$_2$N$_2$O (M+H$^+$) 3.01, found 301.3.

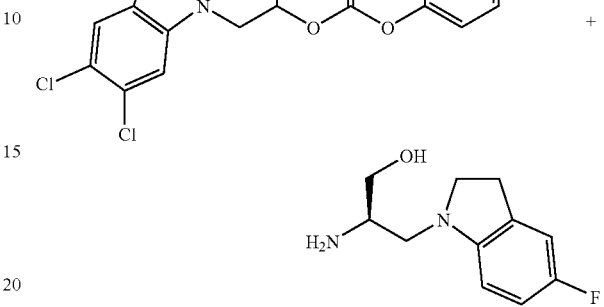

Step C: Synthesis of 1-(5,6-dichloro-benzimidazol-1-yl-methyl)-3,3-dimethyl-butyl 4-nitrophenyl carbonate. The product from step B (445 mg, 1.48 mmol) was dissolved in pyridine (4 mL) and CH$_2$Cl$_2$ (2 mL) and treated with 4-nitrophenyl chloroformate (328 mg, 1.62 mmol). The reaction vessel was sealed and heated to 80° C. overnight. After cooling to room temperature, the reaction was diluted with ethyl acetate and extracted with water twice, 1 M aqueous HCl 3 times, water once and saturated aqueous NaCl once. The organics were then dried over MgSO$_4$ and the solvent was removed. The residue was treated with ether, heated to reflux and put in the refrigerator overnight at −10° C. The resulting solid was collected, washed with cold ether and dried to afford 531 mg (77%) of the product as a slightly colored solid: $^1$H NMR (DMSO, 400 MHz) δ 1.01 (s, 9H), 1.66-1.79 (m, 2H), 4.62 (dd, 1H, J=8.2, J$_2$=14.9), 4.70 (dd, 1H, J=3.4, J$_2$=14.9), 5.23-5.32 (m, 1H), 7.11-7.17 (m, 2H), 8.03 (s, 1H), 8.21 (s, 1H), 8.28-8.33 (m, 2H), 8.51 (s, 1H); HPLC-MS calcd. for C$_{21}$H$_{22}$Cl$_2$N$_4$O$_2$ (M+H$^+$) 466.1, found 466.3.

Step D: A flask was charged with (R)-[1-Benzyloxymethyl-2-(5-fluoro-2,3-dihydro-indol-1-yl)-ethyl]-carbamic acid tert-butyl ester (200 mg, 0.50 mmol, prepared according to Reference 2) and 10% Pd/C (10 mg). The material was treated with MeOH (3.5 mL) and 4 M HCl in dioxane (0.5 mL). The atmosphere in the reaction was exchanged for hydrogen by bubbling hydrogen through the solution and a balloon pressure of hydrogen was kept over the stirring reaction for 1 hour. The atmosphere was exchanged back for nitrogen and the reaction was stirred overnight. The catalyst was removed by filtration through celite using MeOH and the solvent was removed to afford the crude amino alcohol which was used without further purification. HPLC-MS calcd. for C$_{11}$H$_{15}$FN$_2$O (M+H$^+$) 211.1, found 211.4.

The flask containing the amino alcohol was charged with the carbonate obtained from Step C (232 mg, 0.50 mmol), DMF (4 mL) and DIEA (374 μL, 2.0 mmol). The reaction was stirred overnight, diluted with ethyl acetate and extracted with 1 M aqueous NaOH three times and water once. The organics were dried over MgSO$_4$ and the solvent was removed. The resulting material was dissolved in hot ethyl acetate and kept in the refrigerator at −10° C. for 2 days. The resulting solid was collected and washed with cold ethyl acetate to afford 80 mg (30%) of the title compound of Example 1 which ran faster on TLC than the other diastereomer. $^1$H NMR (DMSO, 400 MHz) a 0.87 (s, 9H), 1.44 (dd, 1H, J$_1$=9.3, J$_2$=14.7), 1.46-1.53 (m, 1H), 2.62 (dd, 1H, J$_1$=6.6, J$_2$=13.7), 2.79-2.93 (m, 3H), 3.08-3.18 (m, 1H), 3.23 (dd, 1H, J$_1$=8.7, J$_2$=16.2), 3.38-3.49 (m, 1H), 4.25 (dd, 1H, J$_1$=14.5) 4.35 (dd, 1H, J$_1$=3.9, J$_2$=14.6), 4.64-4.72 (m, 1H), 5.09-5.17 (m, 1H), 6.30 (dd, 1H, J$_1$=4.3, J$_2$=8.6), 6.70-6.78 (m, 1H), 6.86 (dd, 1H, J$_1$=2.6, J$_2$=8.6), 6.93 (d, 1H, J=8.5), 7.83 (s, 1H), 7.97 (s, 1H), 8.24 (s, 1H); HPLC-MS calcd. for C$_{26}$H$_{31}$Cl$_2$FN$_4$O$_3$ (M+H$^+$) 537.2, found 537.4.

The filtrate was concentrated and purified on silica gel using a gradient of 0-100% ethyl acetate in hexane to furnish 50 mg (19%) of the title compound of Example 2. $^1$H NMR (DMSO, 400 MHz) δ 0.80 (s, 9H), 1.37 (dd, 1H, J$_1$=9.9, J$_2$=14.5), 1.45-1.51 (m, 1H), 2.76-2.83 (m, 1H), 2.94 (dd, 1H, J$_1$=8.4, J$_2$=13.7), 3.06 (dd, 1H, J$_1$=4.5, J$_2$=13.8), 3.16-3.26 (m, 3H), 3.47-3.57 (m, 1H), 4.28 (dd, 1H, J$_1$=7.0, J$_2$=14.7), 4.40 (dd, 1H, J$_1$=3.9, J$_2$=14.6), 4.66-4.76 (m, 1H), 5.04-5.12 (m, 1H), 6.35 (dd, 1H, J$_1$=4.3, J$_1$=8.6), 6.69-6.76 (m, 1H), 6.84 (dd, 1H, J$_1$=2.5, J$_2$=8.6), 6.96 (d, 1H, J=8.8), 7.92 (s, 1H), 7.96 (s, 1H), 8.26 (s, 1H); HPLC-MS calcd. for $C_{26}H_{31}Cl_2FN_4O_3$ (M+H$^+$) 537.2, found 537.4.

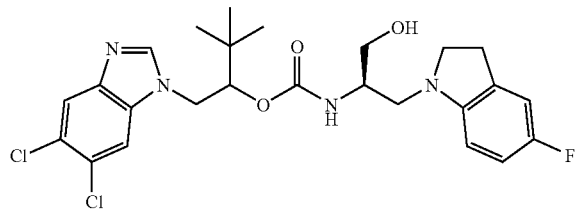

Example 3

1-(5,6-Dichloro-benzimidazol-1-ylmethyl)-2,2-dimethyl-propyl [2-(5-fluoro-2,3-dihydro-indol-1-yl)-1-(R)-hydroxymethyl-ethyl]carbamate

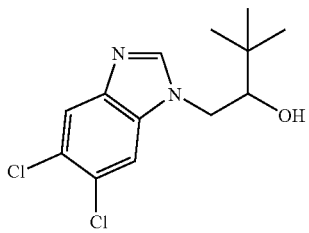

Step A: Preparation of 1-(5,6-Dichloro-benzimidazol-1-yl)-3,3-dimethyl-butan-2-ol. A large (2-5 mL) microwave reactor flask was charged with 5,6-dichlorobenzimidazole (571 mg, 3.1 mmol), 1,2-epoxy-3,3-dimethylbutane (307 mg, 3.1 mmol), powdered anhydrous potassium carbonate (424 mg, 3.1 mmol) and DMF (1.5 mL). The reaction was then heated in a microwave reactor for 6 minutes at 160° C. The reaction was then diluted with ethyl acetate and extracted with water three times. The organics were dried over MgSO$_4$ and the solvent was removed. The residue was crystallized from CH$_2$Cl$_2$ to afford 653 mg (73%) of product as a white solid: $^1$H NMR (DMSO, 400 MHz) δ 1.06 (s, 9H), 3.47 (dd, 1H, J=2.0, J$_2$=10.4), 4.08 (dd, 1H, J$_1$=10.5, J$_2$=14.4), 4.47 (dd, 1H, J$_1$=2.0, J$_2$=14.4), 7.75 (s, 1H), 7.79 (s, 1H), 8.23 (s, 1H); HPLC-MS calcd. for $C_{21}H_{22}Cl_2N_4O_2$ (M+H$^+$) 287.1, found 287.3.

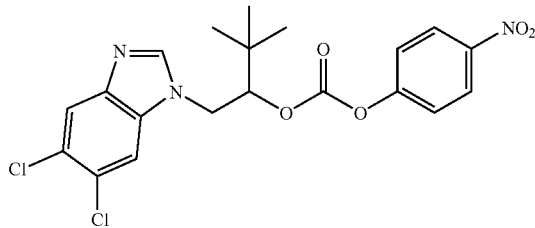

Step B: 1-(5,6-dichloro-benzimidazol-1-ylmethyl)-2,2-dimethyl-propyl 4-nitro-phenyl carbamte. A solution of the product from Step A (100 mg, 0.35 mmol) in dichloroethane (3 mL) was treated with DMAP (90 mg, 0.74 mmol) and 4-nitrophenyl chloroformate (90 mg, 0.45 mmol). The reaction was heated to 80° C. overnight. The reaction was cooled to room temperature, diluted with ethyl acetate and extracted with aqueous 1 M HCl followed by saturated aqueous NaCl. The organics were dried over MgSO$_4$ and the solvent was removed. The residue was purified on silica gel using a linear gradient of 0 to 100% ethyl acetate in hexane to afford 111 mg (70%) of the product as a white solid: $^1$H NMR (MeOD, 400 MHz) δ 1.18 (s, 9H), 4.56 (dd, 1H, J=10.9, J$_2$=15.1), 4.76 (dd, 1H, J$_1$=2.3, J$_2$=15.1), 4.94 (dd, 1H, J$_1$=2.3, J$_2$=10.8), 6.85-6.92 (m, 2H) 7.84 (s, 1H), 7.87 (s, 1H), 8.15-8.21 (m, 2H), 8.38 (s, 1H); HPLC-MS calcd. for $C_{20}H_{19}Cl_2N_3O_5$ (M+H$^+$) 452.1, found 452.2.

Step C: This transformation was performed in an analogous manner to example 1, affording the title compound of example 3 in 66% yield as a mixture of two diastereomers. $^1$H NMR (MeOD, 400 MHz) δ 1.03 (s, 4.5H), 1.10 (s, 4.5H), 2.25 (dd, 0.5H, J$_1$=5.3, J$_2$=13.6), 2.72-2.88 (m, 2.5H), 2.92-3.12 (m, 1.5H), 3.15-3.36 (m, 2H), 3.49-3.56 (m, 2H), 4.30 (dd, 0.5H, J$_1$=8.1, J$_2$=10.8), 4.34 (dd, 0.5H, J$_1$=8.0, J$_2$=10.7), 4.55-4.63 (m, 1H), 4.79 (dd, 0.5H, J$_1$=2.3, J$_2$=10.7), 4.90 (dd, 0.5H, J$_1$=2.5, J$_2$=10.9), 6.25 (dd, 0.5H, J$_1$=4.3, J$_2$=8.5), 6.38 (dd, 0.5H, J=4.2, J$_2$=8.5), 6.61-6.70 (m, 1H), 6.72-6.79 (m, 1H), 7.63 s, 0.5H), 7.77 (s, 0.5H), 7.78 (s, 1H), 8.20 (s, 0.5H), 8.23 (s, 0.5H); HPLC-MS calcd. for $C_{25}H_{29}Cl_2FN_4O_3$ (M+H$^+$) 523.2, found 523.4.

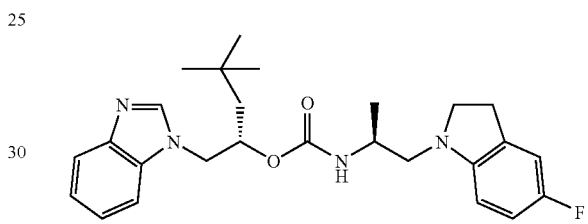

Example 4

1-(S)-(Benzimidazol-1-ylmethyl-3,3-dimethyl)-butyl [2-(5-fluoro-2,3-dihydro-indol-1-yl)-1-(S)-methyl-ethyl]carbamate

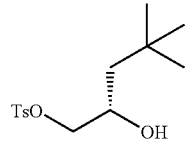

Step A: (S)-2-hydroxy-4,4-dimethylpentanoic acid (2.13 g, 14.6 mmol) was dissolved in tetrahydrofuran (50 mL) and cooled to ice bath temperature. A 1 M solution of BH$_3$ in THF (29.2 mL, 29.2 mmol) was added over ~3 minutes via syringe. After completion of the addition, the cooling bath was removed and the reaction mixture was stirred at room temperature for 4 hours. A 1 M solution of NaOH (100 mL) was added and the reaction is stirred overnight. The reaction is transferred to a separatory funnel and the aqueous layer was extracted 3 times with ethyl acetate. The combined organics were dried over MgSO$_4$ and the solvent was removed. The resulting oil was purified by silica gel chromatography using 0-100% ethyl acetate in hexane to afford 1.63 g (85%) of the diol as an oil. All of this material (12.4 mmol) was dissolved in CH$_2$Cl$_2$ and treated with pyridine (1.96 g, 24.6 mmol) and cooled to ice bath temperature. The mixture was then treated with p-toluenesulfonyl chloride (2.60 g, 13.6 mmol) and stirred overnight while allowing the temperature to raise to ambient. The reaction was then charged to a separatory funnel and extracted 3 times with $CH_2Cl_2$. The combined organics were dried over $MgSO_4$ and the solvent was removed. The resulting oil was carefully purified over silica gel using a gradient of 0 to 100% ethyl acetate in hexane to afford 1.5 g (42%) of (S)-toluene-4-sulfonic acid 2-hydroxy-4,4-dimethyl-pentyl ester; HPLC-MS calcd. for $C_{14}H_{22}O_4S$ (M+H$^+$) 286.1, found 286.4.

Step B: (S)-Toluene-4-sulfonic acid 2-hydroxy-4,4-dimethyl-pentyl ester (355 mg, 1.24 mmol) obtained from Step A, $K_2CO_3$ (429 mg, 3.10 mmol), benzimidazole (191 mg, 1.61 mmol) and DMF (2 mL) were charged to a large microwave reactor vessel. The vessel was crimped shut and heated in the microwave reactor at 160° C. for 6 minutes. The reaction was diluted with ethyl acetate and extracted with 1 M aqueous NaOH three times. The organics were dried over $MgSO_4$ and the solvent was removed to afford 270 mg of crude product that was used without further purification.

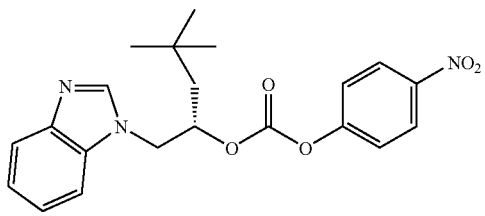

Step C: Preparation of (S)-1-(benzimidazol-1-ylmethyl)-3,3-dimethyl-butyl 4-nitro-phenyl carbamte. The material from the last step was dissolved in pyridine (4 mL) and 4-nitrophenyl chloroformate (325 mg, 1.61 mmol). The reaction was heated to 60° C. for 2.5 hours and 40° C. overnight. The solvent was removed by rotary evaporation and the reaction was partitioned between ethyl acetate and water. The organics were extracted a total of 2 times with water and dried over $MgSO_4$. The solvent was removed and the resulting oil was chromatographed over silica gel using a linear gradient of 0-100% ethyl acetate in hexane to afford 135 mg (27%) of the title compound as a solid; HPLC-MS calcd. for $C_{21}H_{23}N_3O_5$ (M+H$^+$) 398.2, found 398.4.

Step D: This transformation was performed in an analogous manner to example 1, affording the title compound of Example 4 in 85% yield: $^1$H NMR (CDCl$_3$, 400 MHz) δ 0.84 (s, 9H), 1.08 (d, 1H, J=8.6), 1.35-1.43 (m, 1H), 1.53 (dd, 1H, J=9.1, J$_2$=14.5), 2.80-2.91 (m, 3H), 2.97 (dd, 1H, J=7.0, J$_2$=13.4), 3.23 (dd, 1H, J=8.5, J$_2$=17.3), 3.36 (dd, 1H, J$_1$=8.4, J$_2$=16.9), 3.68-3.78 (m, 1H), 4.42 (dd, 1H, J=6.7, J$_2$=14.3), 6.27 (dd, 1H, J$_1$=4.1, J$_2$=8.5), 6.60-6.68 (m, 1H), 6.69-6.77 (m, 1H), 7.45-7.54 (m, 3H), 7.56-7.62 (m, 1H), 7.92-7.99 (m, 1H), 9.58 (s, 1H); HPLC-MS calcd. for $C_{26}H_{33}FN_4O_2$ (M+H$^+$) 453.3, found 453.5.

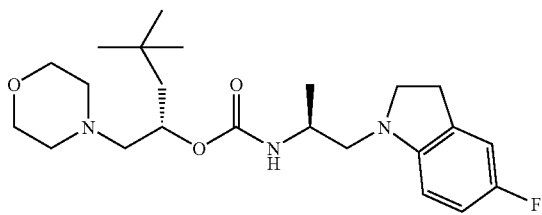

Example 5

3,3-Dimethyl-(S)-1-morpholin-4-ylmethyl-butyl [2-(5-fluoro-2,3-dihydro-indol-1-yl)-1-(S)-methyl-ethyl]carbamate

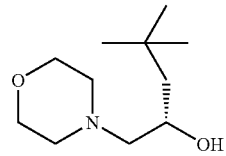

Step A: Preparation of (S)-4,4-dimethyl-1-morpholin-4-yl-pentan-2-ol. (S)-toluene-4-sulfonic acid 2-hydroxy-4,4-dimethyl-pentyl ester obtained from Example 4, step A (700 mg, 2.4 mmol) was charged to a large microwave reactor vial and treated with morpholine (3 mL). The vial was crimped shut and heated to 160° C. for 6 minutes. The solvent was then removed. The resulting oil was dissolved in ethyl acetate and extracted 3 time with aqueous 1 M HCl. The organics were discarded and the aqueous layer was made basic with solid NaOH and extracted 3 times with ethyl acetate. The organic extracts were combined, dried over $MgSO_4$ and the solvent was removed to afford 330 mg (67%) of material which was used without further purification: HPLC-MS calcd. for $C_{11}H_{23}NO_2$ (M+H$^+$) 202.2, found 202.5.

Steps B: A flamed dried 25 ml round bottom flask was charged with triphosgene (28 mg, 95 μmol) and dichloromethane (1 mL). The flask was cooled to −78° C. and a solution of (S)-4,4-dimethyl-1-morpholin-4-yl-pentan-2-ol obtained from Step A (71.5 mg, 0.36 mmol) in dichloromethane (1 mL) was added dropwise. After completion of the addition, the cooling bath was replaced with an ice/water bath and the reaction was allowed to stir for 15 minutes. A solution of (S)-2-(5-fluoro-2,3-dihydro-indol-1-yl)-1-methyl-ethylamine (100 mg, 0.24 mmol, prepared according to Reference 1) in dichloromethane (1 mL) was added followed by excess diisopropylethylamine and the cooling bath was removed. The reaction was stirred for 1.5 h and worked up by introducing aqueous 1 M NaOH and extracting the aqueous layer 3 times with dichloromethane. The organics were dried over $MgSO_4$ and the solvent was removed. The resulting oil was purified by silica gel chromatography using a linear gradient of 0-10% MeOH in dichloromethane to afford 8.1 mg (8.1%) of the desired material as an oil: $^1$H NMR (CDCl$_3$, 400 MHz) δ 0.83 (s, 9H), 1.18 (d, 1H, J=6.6), 1.30-1.46 (m, 2H), 1.48-1.62 (m, 1H), 2.15 (dd, 1H, J=5.9, J$_2$=12.4), 2.31-2.42 (m, 3H), 2.43-2.52 (m, 2H), 2.86 (dd, 2H, J$_1$=J$_2$=8.1), 2.83-2.90 (m, 1H), 2.97 (dd, 1H, J=6.3, J$_2$=13.6), 3.26 (dd, 1H, J=8.6, J$_2$=17.1), 3.36 (dd, 1H, J=8.2, J$_2$=16.4), 3.54-3.61 (m, 4H), 3.81-3.90 (m, 1H), 4.56-4.63 (m, 1H), 4.90-4.99 (m, 1H), 6.28 (dd, 1H, J=4.2, J$_2$=8.5), 6.62-6.68 (m, 1H), 6.71-6.75 (m, 1H); HPLC-MS calcd. for $C_{23}H_{26}FN_3O_3$ (M+H$^+$) 422.3, found 422.6.

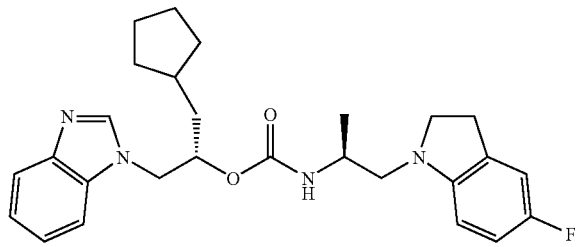

Example 6

2-(Benzimidazol-1-yl)-1-(S)-cyclopentylmethyl-ethyl [2-(5-fluoro-2,3-dihydro-indol-1-yl)-1-(S)-methyl-ethyl]carbamate

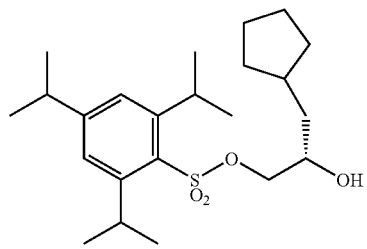

Step A: Preparation of (S)-2,4,6-Triisopropyl-benzenesulfonic acid 3-cyclopentyl-2-hydroxy-propyl ester. A flask was charged with t-BuOH (250 mL), water (250 mL), (DHQ)$_2$PYR (440 mg, 0.50 mmol), K$_3$Fe(CN)$_6$ (49.5 g, 0.15 mol), K$_2$CO$_3$ (21 g, 0.15 mol) and K$_2$OsO$_4$·2H$_2$O (70 mg, 0.19 mmol) and stirred until most of the salts dissolved. The flask was then cooled to 4° C. and allyl cyclopentane (5 g, 45 mmol) was added. The reaction was stirred overnight at 4° C. and quenched by addition of Na$_2$SO$_3$ (50 g). After stirring at room temperature for 1.5 hours, the volatiles were removed in vacuo. The resulting material was partitioned between ethyl acetate and water. The aqueous layer was extracted with ethyl acetate twice more and the combined organics were dried over MgSO$_4$ and the solvent was removed. The resulting oil was chromatographed over silica using 80% ethyl acetate in hexane to afford 4.81 g (74% of diol). A sample (1.21 g, 8.4 mmol) of this material was dissolved in dichloromethane (20 mL) and treated with pyridine (1.44 g, 18 mmol). The reaction was then cooled to ice bath temperature and treated with 2,4,6-triisopropylbenzenesulfonyl chloride (2.83 g, 9.3 mmol). The reaction was allowed to slowly come to room temperature and stirred for 3 days. A solution of 1 M aqueous HCl was added and the reaction was extracted with dichloromethane twice. The combined organics were dried over MgSO$_4$ and the solvent was removed. The residue was purified using silica gel chromatography to afford 1.75 g (51%) of a white powder. The material was crystallized by dissolving in warm hexane and cooling to −4° C. overnight. The mass recovery was 75%: $^1$H NMR (CDCl$_3$, 400 MHz) δ 0.92-1.08 (m, 2H), 1.15 (dd, 1H, J=5.5, J$_2$=6.8), 1.17-1.22 (m, 18H), 1.27-1.36 (m, 2H), 1.40-1.57 (m, 5H), 1.64-1.76 (m, 2H), 1.78-1.90 (m, 1H), 2.80-2.90 (m, 1H), 3.82-3.89 (m, 2H), 3.97-4.10 (m, 3H), 7.13 (s, 2H); HPLC-MS calcd. for C$_{23}$H$_{38}$O$_4$S (M+H$^+$) 411.3, found 411.4.

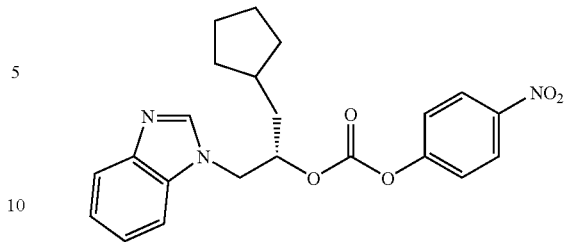

Steps B: 2-(benzimidazol-1-yl)-1-(S)-cyclopentylmethyl-ethyl 4-nitro-phenyl carbonate was prepared in a manner analogous to Example 4, steps B and C. The overall yield was 9%: HPLC-MS calcd. for C$_{22}$H$_{23}$N$_3$O$_5$ (M+H$^+$) 410.2, found 410.3.

Step C: The product of Step B (28 mg, 68 μmol) and (S)-2-(5-fluoro-2,3-dihydro-indol-1-yl)-1-methyl-ethylamine (29 mg, 69 μmol, prepared according to Reference 1) were dissolved in DMF (1 mL) and treated with DIEA (30 mg, 0.23 mmol). The reaction mixture was heated to 60° C. for 3 days, at which time the coupling was nearly complete but HPLC-MS indicated the indoline moiety being oxidized to the indole. The reaction was diluted with ethyl acetate and extracted with water 3 times. The organics were dried over MgSO$_4$ and the solvent was removed. The residue was dissolved in AcOH (0.5 mL) and treated with NaCNBH$_3$ (3 mg, 48 μmol). After 1 hour, the reaction was diluted with ethyl acetate and extracted twice with 1 M aqueous NaOH. The organics were dried over MgSO$_4$ and the solvent was removed. The residue was purified on silica gel using a linear gradient of 50-100% ethyl acetate in hexane to afford 10 mg (31%) of the title compound as an oil: $^1$H NMR (MeOD, 400 MHz) δ 0.96 (d, 3H, J=6.7), 1.03-1.16 (m, 3H), 1.37-1.47 (m, 3H), 1.49-1.83 (m, 9H), 2.77 (dd, 1H, J=5.4, J$_2$=13.6), 2.78-2.88 (m, 3H), 2.94 (dd, 1H, J$_1$=8.1, J$_2$=13.6), 3.17 (dd, 1H, J=8.7, J$_2$=17.4), 3.37-3.46 (m, 1H), 3.55-3.64 (m, 1H), 4.42 (dd, 1H, J=8.9, J$_2$=14.7), 4.61 (dd, 1H, J=3.1, J$_2$=14.7), 5.09-5.18 (m, 1H), 6.34 (dd, 1H, J$_1$=4.2, J$_2$=8.5), 6.60-6.67 (m, 1H), 6.69-6.75 (m, 1H), 7.52-7.59 (m, 2H), 7.78-7.88 (m, 2H), 8.77 (s, 1H); HPLC-MS calcd. for C$_{27}$H$_{33}$FN$_4$O$_2$ (M+H$^+$) 465.3, found 465.4.

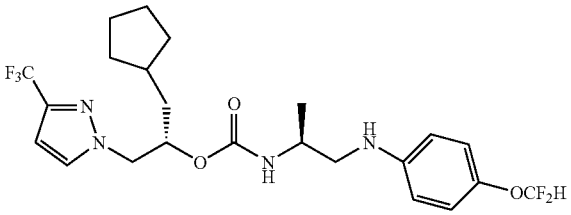

Example 7

1-(S)-Cyclopentylmethyl-2-(3-trifluoromethyl-pyrazol-1-yl)-ethyl [2-(4-difluoromethoxy-phenylamino)-1-(S)-methyl-ethyl]carbamate The title compound was prepared in an analogous fashion to Example 6. $^1$H NMR (CDCl$_3$, 400 MHz) δ 0.93-1.20 (m, 5H), 1.36-1.60 (m, 6H), 1.60-1.82 (m, 3H), 2.90-3.10 (m, 2H), 4.15-4.37 (m, 2H), 4.47-4.62 (m, 1H), 4.99-5.06 (m, 0.5H), 5.13-5.21 (m, 0.5H), 6.29 (dd, 1H, J=J$_2$=74.9), 6.42-

6.51 (m, 3H), 6.84-6.92 (m, 2H), 7.35-7.46 (m, 1H); HPLC-MS calcd. for $C_{23}H_{29}F_5N_4O_3$ (M+H$^+$) 505.2, found 505.4.

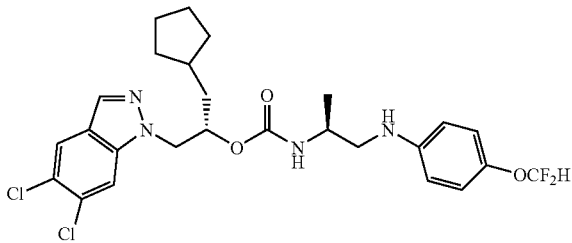

Example 8

1-(S)-Cyclopentylmethyl-2-(5,6-dichloro-benzimidazol-1-yl)-ethyl [2-(4-difluoromethoxy-phenylamino)-1-(S)-methyl-ethyl]carbamate

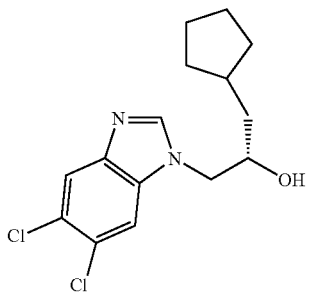

Step A: Preparation of(S)-1-cyclopentyl-3-(5,6-dichloro-benzimidazol-1-yl)-propan-2-ol. Two large (2-5 mL) microwave reactor tubes were charged with (S)-2,4,6-Triisopropyl-benzenesulfonic acid 3-cyclopentyl-2-hydroxy-propyl ester (Example 6, Step A, 1.88 g, 4.6 mmol), 5,6-dichlorobenzimidazole (859 mg, 4.6 mmol), K$_2$CO$_3$ (1.27 g, 9.2 mmol) and DMF (4 mL). The tubes were then heated to 160° C. for 6 minutes. The reaction was partitioned between ethyl acetate and water. The aqueous layer was extracted a total of 2 times with ethyl acetate and the combined organics were dried over MgSO$_4$. The solvent was removed and the resulting oil was chromatographed over silica gel using a linear gradient of 0-100% ethyl acetate in hexane to afford 566 mg (40%) of the title compound as a solid: HPLC-MS calcd. for $C_{15}H_{18}Cl_2N_2O$ (M+H$^+$) 313.1, found 313.2.

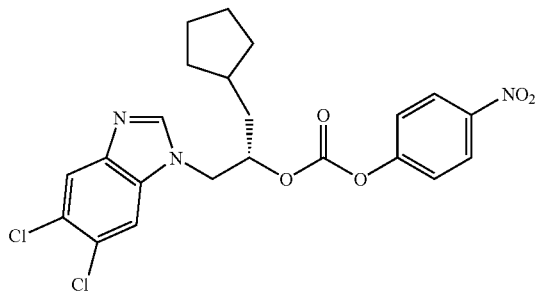

Step B: 1-(S)-cyclopentylmethyl-2-(5,6-dichloro-benzimidazol-1-yl)-ethyl 4-nitro-phenyl carbonate was prepared in 18% yield an analogous fashion to example 1. $^1$H NMR (CDCl$_3$, 400 MHz) δ 1.03-1.21 (m, 2H), 1.47-1.66 (m, 5H), 1.76-1.95 (m, 4H), 4.26 (dd, 1H, J=7.8, J$_2$=15.2), 4.34 (dd, 1H, J=3.7, J$_2$=15.2), 5.04-5.12 (m, 1H), 7.06-7.11 (m, 2H), 7.52 (s, 1H), 7.85 (s, 1H), 7.89 (s, 1H), 8.14-8.19 (m, 2H); HPLC-MS calcd. for $C_{22}H_{21}Cl_2N_3$ (M+H$^+$) 478.1, found 478.2.

Step C: The title compound of Example 8 was prepared in an analogous manner to example 1, affording the product in 39% yield. $^1$H NMR (CDCl$_3$, 400 MHz) a 0.92-1.10 (m, 2H), 1.08 (d, 1H, J=6.7), 1.37-1.58 (m, 6H), 1.61-1.82 (m, 3H), 2.90-3.10 (m, 2H), 3.70-3.82 (m, 1H), 4.08 (dd, 1H, J$_1$=6.3, J$_2$=15.0), 4.25 (dd, 1H, J$_1$=3.6, J$_2$=14.9), 4.72 (d, 1H, J=8.1), 4.99-5.07 (m, 1H), 6.29 (dd, 1H, J=J$_2$=74.8), 6.44-6.50 (m, 2H), 6.84-6.89 (m, 2H), 7.45 (s, 1H), 7.76 (s, 1H), 7.79 (s, 1H); HPLC-MS calcd. for $C_{26}H_{30}Cl_2F_2N_4O_3$ (M+H$^{30}$) 555.2, found 555.3.

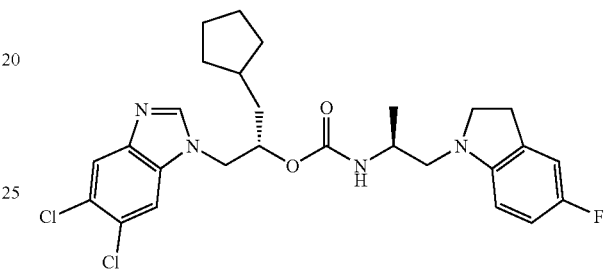

Example 9

1-(S)-cyclopentylmethyl-2-(5,6-dichloro-benzimidazol-1-yl)-ethyl [2-(5-fluoro-2,3-dihydro-indol-1-yl)-1-(S)-methyl-ethyl]carbamate 1-(S)-cyclopentylmethyl-2-(5,6-dichloro-benzimidazol-1-yl)-ethyl 4-nitro-phenyl carbonate (example 8, step C) was converted to the title compound in an analogous manner to example 1 in 69% yield: $^1$H NMR (CDCl$_3$, 400 MHz) δ 0.90-1.07 (m, 2H), 1.08 (d, 1H, J=6.6), 1.32-1.57 (m, 6H), 1.58-1.78 (m, 3H), 2.79-2.98 (m, 4H), 3.21 (dd, 1H, J=8.5, J$_2$=17.1), 3.30-3.79 (m, 1H), 3.71-3.81 (m, 1H), 4.02-4.11 (m, 1H), 4.23 (dd, 1H, J=3.8, J$_2$=15.0), 4.85 (d, 1H, J=7.8), 4.96-5.04 (m, 1H), 6.23 (dd, 1H, J$_1$=3.9, J$_2$=8.3), 6.58-6.66 (m, 1H), 6.68-6.73 (m, 1H), 7.45 (s, 1H), 7.74-7.79 (m, 2H); HPLC-MS calcd. for $C_{27}H_{31}Cl_2FN_4O_2$ (M+H$^+$) 533.2, found 533.3.

Example 10

1-(S)-Cyclopentylmethyl-2-(5,6-dichloro-benzimidazol-1-yl)-ethyl [2-(4-trifluoromethoxy-phenylamino)-1-(S)-methyl-ethyl]carbamate

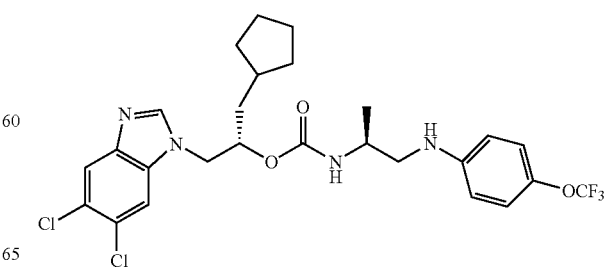

HPLC-MS calcd. for $C_{26}H_{29}Cl_2FN_4O_3$ (M+H$^+$) 573.2, found 573.1.

Example 11

1-(S)-(Benzimidazol-1-ylmethyl-3,3-dimethyl)-butyl [2-(5-fluoro-3,3-dimethyl-2,3-dihydro-indol-1-yl)-1-(S)-methyl-ethyl]carbamate

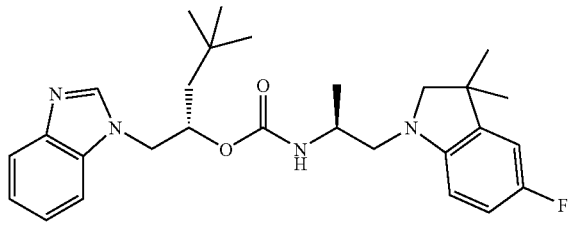

HPLC-MS calcd. for $C_{28}H_{37}FN_4O_2$ (M+H$^+$) 481.3, found 481.3.

Example 12

1-(S)-(Benzimidazol-1-ylmethyl)-3,3-dimethyl-butyl [2-(5-fluoro-2,3-dihydro-indol-1-yl)-1-(R)-hydroxymethyl-ethyl]carbamate

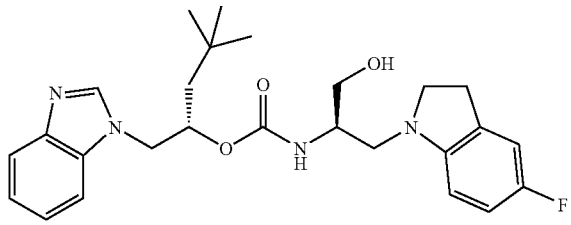

$^1$H NMR (CD$_3$OD, 400 MHz) δ 0.82 (s, 9H), 1.42-1.56 (m, 2H), 2.78-2.88 (m, 2H), 2.96-3.04 (m, 2H), 3.21 (dd, 1H, J=8.7 Hz, J$_2$=17.3 Hz), 3.34-3.42 (m, 3H), 3.62-3.70 (m, 1H), 4.29 (dd, 1H, J=7.1 Hz, J$_2$=14.6 Hz), 5.20-5.28 (m, 1H), 6.38 (dd, 1H, J=4.2 Hz, J$_2$=8.6 Hz), 6.60-6.67 (m, 1H), 7.23-7.28 (m, 1H), 7.28-7.34 (m, 1H), 7.58-7.64 (m, 2H), 8.11 (s, 1H); HPLC-MS calcd. for $C_{26}H_{33}FN_4O_3$ (M+H$^+$) 469.3, found 469.5.

B. Assays for Cathepsin Inhibitory Activity

Cathepsin S

The optimal substrate for cathepsin S, acetyl-histidine-proline-valine-lysine-amino carbamoyl coumarin, was identified from screening a combinatorial library of fluorogenic peptide substrates (Harris, J. L., B. J. Backes, et al. *Proc Natl Acad Sci U S A* 2000, 97(14), 7754-9). Kinetic measurements are performed in a total reaction volume of 30 μl in 384-well microtiter plates. Cathepsin S, at a final concentration of 0.3-3 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 50 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al. *Anal Biochem* 2000, 286(1), 45-50) and are then used to calculate the inhibition constants for competitive inhibitors.

Cathepsin K

The optimal substrate for cathepsin K, acetyl-lysine-histidine-proline-lysine-amino carbamoyl coumarin, was identified from screening a combinatorial library of fluorogenic peptide substrates (Harris, J. L., B. J. Backes, et al. *Proc Natl Acad Sci U S A* 2000, 97(14), 7754-9). Kinetic measurements are performed in a total reaction volume of 30 μl in 384-well microtiter plates. Cathepsin K, at a final concentration of 3.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-lysine-histidine-proline-lysine-amino carbamoyl coumarin, to a final concentration of 40 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al. *Anal Biochem* 2000, 286(1), 45-50) and are then used to calculate the inhibition constants for competitive inhibitors.

Cathepsin L

The optimal substrate for cathepsin L, acetyl-histidine-lysine-phenylalanine-lysine-amino carbamoyl coumarin, was identified from screening a combinatorial library of fluorogenic peptide substrates (Harris, J. L., B. J. Backes, et al. *Proc Natl Acad Sci U S A* 2000, 97(14), 7754-9). Kinetic measurements are performed in a total reaction volume of 30 μl in 384-well microtiter plates. Cathepsin L, at a final concentration of 0.1 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-lysine-phenylalanine-lysine-amino carbamoyl coumarin, to a final concentration of 20 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al. *Anal Biochem* 2000, 286(1), 45-50) and are then used to calculate the inhibition constants for competitive inhibitors.

Cathepsin B

The optimal substrate for cathepsin B, acetyl-histidine-proline-valine-lysine-amino carbamoyl coumarin, was identified from screening a combinatorial library of fluorogenic peptide substrates (Harris, J. L., B. J. Backes, et al. *Proc Natl Acad Sci U S A* 2000, 97(14), 7754-9). Kinetic measurements are performed in a total reaction volume of 30 μl in 384-well microtiter plates. Cathepsin B, at a final concentration of 1.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 10 ™. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al. *Anal Biochem* 2000, 286(1), 45-50) and are then used to calculate the inhibition constants for competitive inhibitors.

Preferred cathepsin S inhibition constants for compounds of the present invention are less than 10 μM. More preferred inhibition constants for compounds of the present invention are less than 1.0 μM. Most preferred inhibition constants for compounds of the present invention are less than 0.1 μM.

Selectivity for cathepsin S in the presence of cathepsin isozymes was determined by the ratio of the cathepsin isozyme inhibition constant of a compound of the present invention to the cathepsin S inhibition constant of the same compound. Preferred compounds of the present invention selective for cathepsin S have ratios of greater than 10. More preferred compounds of the present invention selective for cathepsin S have ratios of greater than 100. Most preferred compounds of the present invention selective for cathepsin S have ratios of greater than 1000.

TABLE I

Assay Data for Inhibitors of Cathepsin S

| Example | $K_i$ Cat. S[a] | Selectivity for Cat. S over Cat. K[b] | Selectivity for Cat. S over Cat. L[b] | Selectivity for Cat. S over Cat. B[b] |
|---|---|---|---|---|
| 1 | + | − | + | + |
| 2 | +++ | ++ | + | +++ |
| 3 | +++ | + | − | + |
| 4 | +++ | + | ++ | +++ |
| 5 | ++ | − | ++ | ++ |
| 6 | +++ | + | ++ | +++ |
| 7 | ++ | + | ++ | ++ |
| 8 | ++ | + | ++ | +++ |
| 9 | +++ | + | + | +++ |
| 10 | +++ | + | + | +++ |
| 11 | +++ | − | ++ | +++ |
| 12 | +++ | − | ++ | +++ |

[a]Cathepsin S inhibition constant for compounds of Formula I: +, <10 μM; ++, <1.0 μM; +++, <0.1 μM.
[b]Selectivity of compounds of Formula I for cathepsin S over another cathepsin: −, <10; +, >10; ++, >100; +++, >1000.

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:

1. A compound having the Formula:

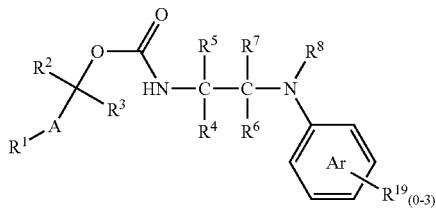

(I)

or a pharmaceutically acceptable salt thereof, wherein:

A is —$CH_2$—, —$CH_2CH_2$— or a bond;

$R^1$ is a benzimidazolyl substituted with 0-3 $R^{1a}$ or a $C_3$-$C_8$ heterocycle containing 1 to 2 heteroatoms each independently a member selected from the group consisting of N, O and S, wherein said heterocycle is substituted with 0-2 $R^{1a}$;

each $R^{1a}$ is independently a member selected from the group consisting of F, Cl, Br, CN, $NO_2$, OH, acetyl, C(=O)$OR^{10}$, C(=O)$NR^{10}R^{11}$, S(=O)$_2NR^{10}R^{11}$; $C_3$-$C_7$ cycloalkyl; —$SCH_3$, —S(=O)$CH_3$, —S(=O)$_2CH_3$, $NR^{12}R^{13}$, $C_1$-$C_6$ alkoxy, $C_1$-$C_3$ perfluoroalkyl, $C_1$-$C_3$ perfluoroalkoxy, a $C_1$-$C_6$ alkyl, phenyl substituted with 0-3 $R^4$, a 5- to 6-membered heteroaryl containing 1 to 4 heteroatoms each independently a member selected from the group consisting of N, O and S, wherein said heteroaryl is substituted with 0-3 $R^4$, a $C_3$-$C_8$ heterocycle containing 1 to 2 heteroatoms each independently a member selected from the group consisting of N, O and S, wherein said heterocycle is substituted with 0-2 $R^4$ and is saturated or partially unsaturated;

$R^2$ is a member selected from the group consisting of a $C_1$-$C_6$ alkyl substituted with 0-2 $R^{2a}$, wherein said $C_1$-$C_6$ alkyl may optionally contain a heteroatom selected from the group consisting of —O—, —S—, —S(=O)— and —S(=O)$_2$—, a $C_2$-$C_6$ alkenyl substituted with 0-1 $R^{2a}$, a $C_3$-$C_6$ alkynyl substituted with 0-1 $R^{2a}$, a $C_3$-$C_7$ cycloalkyl substituted with 0-2 $R^{2b}$, a $C_7$-$C_{11}$ bicycloalkyl substituted with 0-2 $R^{2b}$, phenyl substituted with 0-3 $R^{14}$, a 5- to 6-membered heteroaryl containing 1 to 4 heteroatoms each independently a member selected from the group consisting of N, O and S, wherein said heteroaryl is substituted with 0-3 $R^{14}$;

each $R^{2a}$ is independently a member selected from the group consisting of a $C_6$-$C_{10}$ aryl substituted with 0-3 $R^{14}$, a perfluorophenyl, a $C_3$-$C_8$ cycloalkyl substituted with 0-2 $R^{2b}$, a $C_7$-$C_{11}$ bicycloalkyl substituted with 0-2 $R^{2b}$, and a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{14}$;

each $R^{2b}$ is independently a member selected from the group consisting of H, OH, F, Cl, $C_1$-$C_6$ alkyl, $C_1$-$C_6$ alkoxy, $CF_3$, and $OCF_3$;

$R^3$ is a member selected from the group consisting of H and $C_1$-$C_6$ alkyl;

$R^4$ is a member selected from the group consisting of H, C(=O)$OR^{15}$, C(=O)$NR^{16}R^{17}$, phenyl substituted with 0-2 $R^{14}$, 5- to 6-membered heteroaryl containing 1 to 4 heteroatoms each independently a member selected from the group consisting of N, O and S, wherein said heteroaryl is substituted with 0-2 $R^{14}$, $C_3$-$C_7$ cycloalkyl, $C_1$-$C_6$ alkyl substituted with 0-2 $R^{20}$, wherein said $C_1$-$C_6$ alkyl may optionally contain a heteroatom selected from the group consisting of —O—, —S—, —S(=O)—, —S(=O)$_2$— and —$NR^6$—;

each of $R^5$, $R^6$, $R^7$ and $R^8$ is independently a member selected from the group consisting of H and $C_1$-$C_6$ alkyl;

alternatively, $R^4$ and $R^6$ are taken together to form a $C_5$-$C_7$ cycloalkyl;

each of $R^{10}$ and $R^{11}$ is independently a member selected from the group consisting of H, and $C_1$-$C_4$ alkyl;

alternatively, $R^{10}$ and $R^{11}$ on the same nitrogen are taken together to form a 5- to 7-membered heterocyclic ring containing 1-2 heteroatoms each independently a member selected from the group consisting of N, O and S;

each $R^{12}$ is independently a member selected from the group consisting of H, $C_1$-$C_4$ alkyl, ($C_1$-$C_4$ alkyl)-C(=O)— and ($C_1$-$C_4$ alkyl)-S(=O)$_2$—;

each $R^{13}$ independently a member selected from the group consisting of H and $C_1$-$C_4$ alkyl;

alternatively, $R^{12}$ and $R^{13}$ on the same nitrogen are taken together to form a 5- to 7-membered heterocyclic ring containing 1-2 heteroatoms each independently a member selected from the group consisting of N, O and S;

each $R^{14}$ independently a member selected from the group consisting of H, OH, F, Cl, Br, CN, NO$_2$, COOR$^{10}$, C(=O)NR$^{10}$R$^{11}$, S(=O)$_2$NR$^{10}$R$^{11}$, acetyl, —SCH$_3$, —S(=O)CH$_3$, —S(=O)$_2$CH$_3$, NR$^{12}$R$^{13}$, $C_1$-$C_6$ alkoxy, $C_1$-$C_3$ perfluoroalkyl, $C_1$-$C_3$ perfluoroalkoxy, and a $C_1$-$C_6$ alkyl;

each $R^{15}$ is independently a member selected from the group consisting of H, $C_3$-$C_7$ cycloalkyl, $C_1$-$C_4$ alkyl substituted with 0-1 $R^{18}$, and a phenyl substituted with 0-3$R^{14}$;

each $R^{16}$ is independently a member selected from the group consisting of H, $C_3$-$C_8$ cycloalkyl, a phenyl substituted with 0-3 $R^{14}$, and a $C_1$-$C_6$ alkyl substituted with 0-1 $R^{18}$;

each $R^{17}$ is independently a member selected from the group consisting of H and $C_1$-$C_4$ alkyl;

alternatively, $R^{16}$ and $R^{17}$ on the same N atom are taken together to form a $C_5$-$C_7$ heterocycle containing 1-2 heteroatoms each independently a member selected from the group consisting of N, O and S.

each $R^{18}$ is independently a member selected from the group consisting of H, $C_3$-$C_7$ cycloalkyl, a phenyl substituted with 0-3 $R^{14}$ and a 5- to 6-membered heteroaryl containing 1 to 4 heteroatoms each independently a member selected from the group consisting of N, O and S, wherein said 5- to 6-membered heteroaryl is substituted with 0-3 $R^{14}$;

each $R^{19}$ is independently a member selected from the group consisting of H, F, Cl, Br, CN, OR$^{21}$, SCH$_3$, S(=O)CH$_3$, S(=O)$_2$CH$_3$, S(=O)$_2$NR$^{10}$R$^{11}$, NR$^{12}$R$^{13}$, acetyl, C(=O)NR$^{10}$R$^{11}$, CO$_2$R$^{10}$, C(=NH)NH$_2$, $C_1$-$C_6$ alkyl, CF$_3$; and a 5- to 6-membered heteroaryl containing 1 to 4 heteroatoms each independently a member selected from the group consisting of N, O and S, wherein said heteroaryl is substituted with 0-3 $R^{14}$;

alternatively, $R^{19}$ and $R^8$ are taken together to form a 5- to 7-membered heterocyclic ring containing 1-2 heteroatoms, each independently a member selected from the group consisting of N, O and S, wherein said 5 to 7 membered heterocyclic ring is ortho-fused to Ar and wherein said 5- to 7-membered heterocyclic ring may be optionally substituted with 0-2 $R^{22}$;

each $R^{20}$ is independently a member selected from the group consisting of H, OH, F, Cl, CN, NO$_2$, C(=O)OR$^{15}$, C(=O)NR$^{16}$R$^{17}$, NR$^{12}$R$^{13}$, $C_1$-$C_3$ perfluoroalkoxy, $C_1$-$C_3$ perfluoroalkyl, $C_1$-$C_4$ alkoxy, $C_2$-$C_4$ alkenyl, $C_2$-$C_4$ alkynyl, phenyl substituted with 0-3 $R^{14}$, 5- to 6-membered heteroaryl containing 1 to 4 heteroatoms each independently a member selected from the group consisting of N, O and S, wherein said heteroaryl is substituted with 0-3 $R^4$, $C_3$-$C_8$ heterocycle containing 1 to 2 heteroatoms each independently a member selected from the group consisting of N, O and S, wherein said heterocycle is substituted with 0-2 $R^{14}$ and is saturated or partially unsaturated, and $C_3$-$C_8$ cycloalkyl;

each $R^{21}$ is independently a member selected from the group consisting of H, CF$_3$, CHF$_2$, $C_1$-$C_6$ alkyl, $C_3$-$C_8$ cycloalkyl, a phenyl substituted with 0-3 $R^{14}$, a 5- to 6-memebered heteroaryl containing 1 to 4 heteroatoms each independently a member selected from the group consisting of N, O and S, wherein said 5- to 6-membered heteroaryl is substituted with 0-3 $R^{14}$, and a CH$_2$ substituted with 1 $R^{18}$; and each $R^{22}$ is independently a member selected from the group consisting of $C_1$-$C_4$ alkyl, F, Cl and $C_1$-$C_4$ alkoxy, CF$_3$ and OCF$_3$, or alternatively, two $R_{22}$ may be combined to form $C_3$-$C_6$ cycloalkyl.

2. The compound of claim 1, wherein said compound has the formula:

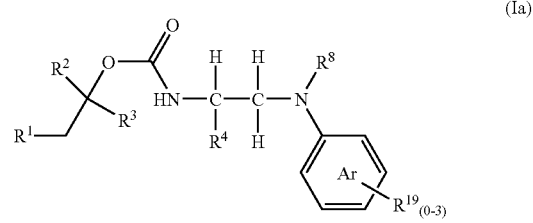

(Ia)

wherein $R^3$ is H;

$R^8$ and $R^{19'}$ are independently H or $C_{1-6}$ alkyl;

or $R^8$ together with $R^{19'}$ form a 5- to 7-membered ring that is fused to Ar and wherein said 5- to 7-membered heterocyclic ring may be optionally substituted with 0-2 $R^{22}$.

3. The compound of claim 2, wherein $R^2$ is a member selected from the group consisting of a $C_1$-$C_6$ alkyl substituted with 0-1 $R^{2a}$, a $C_3$-$C_7$ cycloalkyl substituted with 0-2 $R^{2b}$, a $C_7$-$C_{11}$ bicycloalkyl substituted with 0-2 $R^{2b}$, and phenyl substituted with 0-3 $R^{14}$; and each $R^{2a}$ is independently a member selected from the group consisting of a $C_6$-$C_{10}$ aryl substituted with 0-3 $R^{14}$, a $C_3$-$C_8$ cycloalkyl substituted with 0-2 $R^{2b}$, and a $C_7$-$C_{11}$ bicycloalkyl substituted with 0-2 $R^{2b}$.

4. The compound of claim 3, wherein $R^2$ is selected from the group consisting of $C_1$-$C_6$ alkyl, and $C_1$-$C_4$ alkyl substituted with 1 $R^{2a}$; and $R^{2a}$ is selected from the group consisting of $C_3$-$C_7$ cycloalkyl substituted with 0-2 $R^{2b}$, and a $C_7$-$C_{11}$ bicycloalkyl substituted with 0-2 $R^{2b}$.

5. The compound of claim 1, wherein $R^1$ is a member selected from group consisting of morpholinyl, pyrrolidinyl, piperidinyl, piperazinyl, pyrazolyl, imidazolyl, 1,3,4-oxadiazolyl, or benzimidazolyl, benzothiazolyl, and benzoxazolyl substituted with 0-3 $R^{1a}$.

6. The compound of claim 2, wherein $R^4$ is a member selected from the group consisting of H, $C_3$-$C_7$ cycloalkyl, $C_1$-$C_6$ alkyl substituted with 0R$^{20}$, wherein said $C_1$-$C_6$ alkyl may optionally contain a heteroatom selected from the group consisting of —O—, —S—, —S(=O)$_2$—;

each $R^{20}$ is independently a member selected from the group consisting of H, OH, C(=O)OR$^{15}$, C(=O)NR$^{16}$R$^{17}$, NR$^{12}$R$^{13}$, phenyl substituted with 0-3 $R^{14}$, 5- to 6-membered heteroaryl containing 1 to 4 heteroatoms each independently a member selected from the group consisting of N, O and S, wherein said heteroaryl is substituted with 0-3 $R^{14}$, $C_3$-$C_8$ heterocycle containing 1 to 2 heteroatoms each independently a member selected from the group consisting of N, O and S, wherein said heterocycle is substituted with 0-2 $R^{14}$ and is saturated or partially unsaturated, and $C_3$-$C_8$ cycloalkyl; and $R^{19}$ and $R^8$ are taken together to form a 5- to 7-membered heterocyclic ring containing 1 nitrogen wherein said 5 to 7 membered heterocyclic ring is ortho-fused to Ar; and may be optionally substituted with 0-2 $R^{22}$.

7. The compound of claim 6, wherein
$R^1$ is selected from group consisting of morpholinyl, pyrazolyl, and benzimidazolyl, substituted with 0-3 $R^{1a}$;
$R^2$ is selected from the group consisting of $C_1$-$C_6$ alkyl, and $C_1$-$C_2$ alkyl substituted with 1 $R^{2a}$; and
$R^{2a}$ is selected from the group consisting of $C_3$-$C_7$ cycloalkyl substituted with 0-2 $R^{2b}$;
$R^4$ is a member selected from the group consisting of H, $C_3$-$C_5$ cycloalkyl, $C_1$-$C_6$ alkyl substituted with 0-1$R^{20}$, wherein said $C_1$-$C_6$ alkyl may optionally contain a heteroatom selected from the group consisting of —O—, —S—, —S(=O)$_2$—; and
each $R^{20}$ is independently a member selected from the group consisting of H, OH, C(=O)O$R^{15}$, C(=O)N$R^{16}R^{17}$, N$R^{12}R^{13}$, and phenyl substituted with 0-3 $R^{14}$.

8. The compound of claim 6, wherein

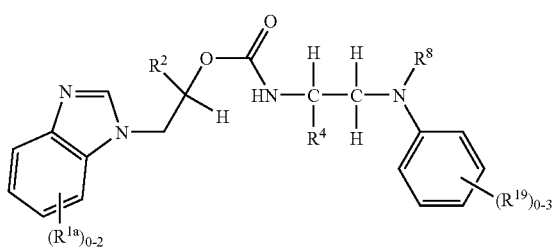

Ib wherein:
each $R^{1a}$ is independently a member selected from the group consisting of F, Cl, Br, $C_1$-$C_6$ alkoxy, $C_1$-$C_3$ perfluoroalkyl, $C_1$-$C_3$ perfluoroalkoxy, a $C_1$-$C_6$ alkyl;
$R^4$ is a member selected from the group consisting of H, CH$_2$CO$_2R^{15}$, $C_1$-$C_6$ alkyl, cyclopropyl, benzyloxymethyl, benzyl, phenethyl, methanesulfonylmethyl, methylsulfonylethyl and ($C_1$-$C_4$ alkyl)-OH;
each $R^{15}$ is independently a member selected from the group consisting of H and $C_1$-$C_4$ alkyl.

9. The compound of claim 8, wherein said compound has the formula

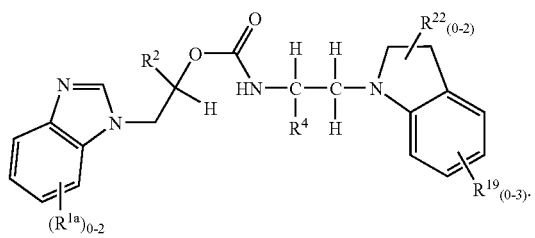

Ic

10. The compound of claim 1, wherein said compound is selected from the group consisting of
1-(R)-(5,6-dichloro-benzimidazol-1-ylmethyl)-3,3-dimethyl-butyl [2-(5-fluoro-2,3-dihydro-indol-1-yl)-1-(R)-hydroxymethyl-ethyl] carbamate;
1-(S)-(5,6-dichloro-benzimidazol-1-ylmethyl)-3,3-dimethyl-butyl [2-(5-fluoro-2,3-dihydro-indol-1-yl)-1-(R)-hydroxymethyl-ethyl] carbamate;
1-(5,6-dichloro-benzimidazol-1-ylmethyl)-2,2-dimethylpropyl [2-(5-fluoro-2,3-dihydro-indol-1-yl)-1-(R)-hydroxymethyl-ethyl] carbamate;
1-(S)-(benzimidazol-1-ylmethyl-3,3-dimethyl)-butyl [2-(5-fluoro-2,3-dihydro-indol-1-yl)-1-(S)-methyl-ethyl] carbamate;
3,3-dimethyl-(S)-1-morpholin-4-ylmethyl-butyl [2-(5-fluoro-2,3-dihydro-indol-1-yl)-1-(S)-methyl-ethyl] carbamate;
2-(benzimidazol-1-yl)-1-(S)-cyclopentylmethyl-ethyl [2-(5-fluoro-2,3-dihydro-indol-1-yl)-1-(S)-methyl-ethyl] carbamate;
1-(S)-cyclopentylmethyl-2-(3-trifluoromethyl-pyrazol-1-yl)-ethyl [2-(4-difluoromethoxy-phenylamino)-1-(S)-methyl-ethyl] carbamate;
1-(S)-cyclopentylmethyl-2-(5,6-dichloro-benzimidazol-1-yl)-ethyl [2-(4-difluoromethoxy-phenylamino)-1-(S)-methyl-ethyl] carbamate
1-(S)-cyclopentylmethyl-2-(5,6-dichloro-benzimidazol-1-yl)-ethyl [2-(5-fluoro-2,3-dihydro-indol-1-yl)-1-(S)-methyl-ethyl] carbamate;
1-(S)-cyclopentylmethyl-2-(5,6-dichloro-benzimidazol-1-yl)-ethyl [2-(4-trifluoromethoxy-phenylamino)-1-(S)-methyl-ethyl] carbamate;
1-(S)-(benzimidazol-1-ylmethyl-3,3-dimethyl)-butyl [2-(5-fluoro-3,3-dimethyl-2,3-dihydro-indol-1-yl)-1-(S)-methyl-ethyl] carbamate; and
1-(S)-(benzimidazol-1-ylmethyl)-3,3-dimethyl-butyl [2-(5-fluoro-2,3-dihydro-indol-1-yl)-1-(R)-hydroxymethyl-ethyl] carbamate.

11. A pharmaceutical composition, said composition comprising a compound of claim 1 and an excipient.

* * * * *